(12) United States Patent
Park et al.

(10) Patent No.: US 9,395,527 B2
(45) Date of Patent: Jul. 19, 2016

(54) FLUORESCENT MICROSCOPE FOR OBSERVING MULTIPLE FLUORESCENT IMAGES, FLUORESCENT IMAGE SURVEYING METHOD USING THE SAME, AND MULTIPLE FLUORESCENT IMAGE OBSERVING SYSTEM

(75) Inventors: Hwa Joon Park, Seoul (KR); Jeoung Ku Hwang, Seoul (KR); Jee Young Kim, Gueonggi-do (KR); Chan Il Chung, Seoul (KR)

(73) Assignee: NANOTEK, INC., Seoul (KR)

(*) Notice: Subject to any disclaimer, the term of this patent is extended or adjusted under 35 U.S.C. 154(b) by 673 days.

(21) Appl. No.: 13/809,319

(22) PCT Filed: Aug. 18, 2011

(86) PCT No.: PCT/KR2011/006084
§ 371 (c)(1),
(2), (4) Date: Apr. 17, 2013

(87) PCT Pub. No.: WO2012/023816
PCT Pub. Date: Feb. 23, 2012

(65) Prior Publication Data
US 2013/0201322 A1 Aug. 8, 2013

(30) Foreign Application Priority Data
Aug. 18, 2010 (KR) .................. 10-2010-0079932
Aug. 18, 2011 (KR) .................. 10-2011-0082148

(51) Int. Cl.
*G02B 21/00* (2006.01)
*G02B 21/16* (2006.01)
*G01N 21/64* (2006.01)

(52) U.S. Cl.
CPC ........ *G02B 21/0076* (2013.01); *G02B 21/0064* (2013.01); *G02B 21/16* (2013.01); *G01N 2021/6419* (2013.01); *G01N 2021/6421* (2013.01); *G02B 2207/113* (2013.01)

(58) Field of Classification Search
CPC .............. G01N 2021/6419; G01N 2021/6421; G02B 21/0064; G02B 21/0076; G02B 21/16; G02B 2207/113
USPC .......................................................... 348/80
See application file for complete search history.

(56) References Cited

U.S. PATENT DOCUMENTS 5,833,617 A * 11/1998 Hayashi ............. A61B 1/00009
250/461.1
6,075,643 A * 6/2000 Nonoda ............. G02B 21/0088
359/372

(Continued)

FOREIGN PATENT DOCUMENTS

JP 2000-089124 A 3/2000
JP 2004-012966 A 1/2004

(Continued)

OTHER PUBLICATIONS

International Search Report under date of mailing of Mar. 23, 2012 in connection with PCT/KR2011/006084.

(Continued)

*Primary Examiner* — Anner Holder
(74) *Attorney, Agent, or Firm* — Paratus Law Group, PLLC

(57) ABSTRACT

A fluorescent microscope for observing multiple fluorescent images includes: a first optical module comprising a first light source for supplying first excitation light having a first wavelength, a first excitation filter for selectively transmitting the first excitation light supplied from the first light source, a first dichroic filter for reflecting the first excitation light having passed through the first excitation filter toward the survey object, an objective lens for condensing the first excitation light reflected by the first dichroic filter and transferring the condensed first excitation light to the survey object, a second dichroic filter for reflecting first radiation light radiated from the survey object, a first radiation filter for selectively transmitting the first radiation light reflected by the second dichroic filter, and a first image acquisition unit for acquiring an image by using the first radiation light having passed through the first radiation filter to be supplied; and a second optical module comprising a second light source for supplying second excitation light having a second wavelength, a second excitation filter for selectively transmitting the second excitation light supplied from the second light source, a second radiation filter passing through the second excitation filter and irradiated to the survey object to be radiated, to selectively transmitting the second radiation light EM2 having passed through the objective lens, the first dichroic filter, and the second excitation filter, and a second image acquisition unit for acquiring an image by using the second radiation light having passed through the second radiation filter to be supplied.

7 Claims, 20 Drawing Sheets

(56) References Cited

U.S. PATENT DOCUMENTS

| | | | |
|---|---|---|---|
| 2003/0095721 A1* | 5/2003 | Clune | A61B 1/00009 382/294 |
| 2005/0031178 A1 | 2/2005 | Park | |
| 2008/0015446 A1* | 1/2008 | Mahmood | A61B 1/00009 600/476 |
| 2009/0310239 A1* | 12/2009 | Adler | G01N 21/956 359/891 |

FOREIGN PATENT DOCUMENTS

| | | |
|---|---|---|
| JP | 2005017282 A | 1/2005 |
| JP | 2006-220994 A | 8/2006 |
| JP | 2010085826 A | 4/2010 |
| WO | 2009-069675 A1 | 6/2009 |

OTHER PUBLICATIONS

Korean Intellectual Property Office, Notice to File a Response, Patent Application No. 10-2011-0082148, Dec. 20, 2012.

Korean Intellectual Property Office, Notice of Allowance, Patent Application No. 10-2011-0082148, May 30, 2013.

* cited by examiner

FLUORESCENT MICROSCOPE FOR OBSERVING MULTIPLE FLUORESCENT IMAGES, FLUORESCENT IMAGE SURVEYING METHOD USING THE SAME, AND MULTIPLE FLUORESCENT IMAGE OBSERVING SYSTEM

CROSS-REFERENCE TO RELATED APPLICATIONS

This application represents the national stage entry of PCT International Application No. PCT/KR2011/006084 filed Aug. 18, 2011, which claims the benefit of Korean Patent Application No. 10-2010-0079932 filed Aug. 18, 2010, and Korean Patent Application No. 10-2011-0082148 filed Aug. 18, 2011, all of which are hereby incorporated by reference in their entirety.

TECHNICAL FIELD

The present invention relates to a fluorescent microscope for observing multiple fluorescent images, a fluorescent image surveying method using the same, and a multiple fluorescent image observing system, and more particularly, to a fluorescent microscope for observing multiple fluorescent images by which a plurality of fluorescent images can be simply and promptly observed without a mechanical movement, a fluorescent image surveying method using the same, and a multiple fluorescent image observing system.

BACKGROUND ART

A fluorescent microscope refers to an apparatus which processes a fluorescent material (fluorescent pigment) in a sample by using a principle in which fluorescent light is emitted from a fluorescent substance if the fluorescent substance absorbs light having a specific wavelength, and irradiates light having the absorption wavelength of the fluorescent material to the sample to survey the sample through radiation light emitted from the sample. The fluorescent microscope can obtain a clear image as compared with a general optical microscope, and thus is widely used when a sample such as a bio chip is surveyed.

FIG. 1 is a schematic diagram illustrating a general fluorescent microscope according to the related art.

Referring to FIG. 1, the fluorescent microscope according to the related art sorts monochromatic light having the same wavelength as an absorption wavelength of a fluorescent substance attached to a sample 17 positioned on a plate 16 from white light 10 through a first optical filter 11, adjusts a path of the sorted monochromatic light 10a having the absorption wavelength through a dichroic mirror 13 to irradiate the monochromatic light 10a to the sample 17 through an objective lens 12, and sorts light having the same wavelength as a coloring wavelength of the fluorescent substance of the sample 17 from the light 10b generated by the fluorescent substance of the sample 17 having passed the objective lens 12 and the dichroic mirror 13 through a second optical filter 14 to provide the sorted light to a light receiving unit 15. Meanwhile, the light receiving unit 15 is realized by an ocular lens or an image pickup device such as a CCD, and detects the coloring wavelength of the fluorescent substance attached to the sample 17 to allow a shape of the sample 17 to be surveyed.

However, the fluorescent microscope according to the related art is configured to obtain a single fluorescent image according to the light irradiated to the sample 17, and is unsuitable for irradiating various kinds of light to obtain fluorescent images and then comparing the fluorescent images to survey an accurate shape of the sample 17.

Although a multi fluorescent microscope including a plurality of light sources to irradiate various kinds of light to the sample 17 has been developed to solve the problem, the multi fluorescent microscope according to the related art is configured to obtain a fluorescent image through a single light receiving unit 15, and thus has a problem of having to mechanically replace a light source and a filter according to a type of light irradiated to the sample 17.

That is, the multi fluorescent microscope requires separate electronic and mechanical equipment to replace a light source and a filter, requiring high production costs, generates mechanical vibrations, causing a breakdown of the device, and consumes a separate time for replacing a light source and a filter, making it difficult to promptly and simply obtain a desired fluorescent image.

Accordingly, a multi fluorescent microscope capable of simply and promptly obtaining a plurality of fluorescent images without a mechanical movement has been requested to be developed.

DETAILED DESCRIPTION OF THE INVENTION

Technical Problem

Therefore, the present invention has been made in view of the above-mentioned problems, and an aspect of the present invention is to provide a fluorescent microscope for observing multiple fluorescent images by which a plurality of fluorescent images can be simply and promptly observed without a mechanical movement, a fluorescent image surveying method using the same, and a multi fluorescent image observing system.

The technical aspects of the present invention are not limited to the above-mentioned technical aspects, and the other unmentioned technical aspects of the present invention will become clear to those skilled in the art to which the present invention pertains from the following description.

Technical Solution

In accordance with an aspect of the present invention, there is provided a fluorescent microscope for observing multiple fluorescent images, the fluorescent microscope including: a first optical module including a first light source for supplying first excitation light having a first wavelength, a first excitation filter for selectively transmitting the first excitation light supplied from the first light source, a first dichroic filter for reflecting the first excitation light having passed through the first excitation filter toward the survey object, an objective lens for condensing the first excitation light reflected by the first dichroic filter and transferring the condensed first excitation light to the survey object, a second dichroic filter for reflecting first radiation light radiated from the survey object, a first radiation filter for selectively transmitting the first radiation light reflected by the second dichroic filter, and a first image acquisition unit for acquiring an image by using the first radiation light having passed through the first radiation filter to be supplied; and a second optical module including a second light source for supplying second excitation light having a second wavelength, a second excitation filter for selectively transmitting the second excitation light supplied from the second light source, a second radiation filter passing through the second excitation filter and irradiated to the survey object to be radiated, to selectively transmitting the second radiation light EM2 having passed through the objective lens, the first dichroic filter, and the second excitation filter, and a second image acquisition unit for acquiring an image by using the second radiation light having passed through the second radiation filter to be supplied.

The second optical module may further include: a third dichroic filter interposed between the second light source and the survey object, and the fluorescent microscope may further include: a third optical module including: a third light source provided adjacent to the second light source to supply third excitation light having a third wavelength to the survey object such that a bright field image of the survey object is surveyed through the second image acquisition unit, and a fourth dichroic filter disposed in a direction perpendicular to a disposition direction of the third dichroic filter between the third light source and the third dichroic filter to uniformly adjust a brightness of the bright field image.

The first light source may be a blue solid state fluorescence light source, the second light source may be any one of a green solid state fluorescence light source and a red solid state fluorescence light source, and the third light source may be any one of a white solid state fluorescence light source and a red solid state fluorescence light source.

In accordance with another aspect of the present invention, there is provided a fluorescent microscope for observing multiple fluorescent images, the fluorescent microscope including: a first optical module including a first light source for supplying first excitation light having a first wavelength, a first dichroic filter for reflecting the first excitation light supplied from the first light source, an excitation filter for selectively transmitting the first excitation light reflected by the first dichroic filter, a second dichroic filter for reflecting the first excitation light having passed through the first dichroic filter toward the survey object, an objective lens for condensing the first excitation light reflected by the second dichroic filter and transferring the condensed first excitation light to the survey object, a third dichroic filter for reflecting first radiation light radiated from the survey object and passing through the second dichroic filter, a first radiation filter for selectively transmitting the first radiation light reflected by the third dichroic filter, and a first image acquisition unit for acquiring an image by using the first radiation light having passed through the first radiation filter to be supplied; and a second optical module including a second light source disposed adjacent to the first light source to supplying second excitation light having a second wavelength in a direction crossing a progress direction of the first excitation light, a second radiation filter for selectively transmitting second radiation light passing through the first dichroic filter and the excitation filter, reflected by the second dichroic filter, passing the objective lens, irradiated to the survey object to be radiated, and passing through the second dichroic filter and the third dichroic filter, and a second image acquisition unit for acquiring an image by using the second radiation light having passed through the second radiation filter to be supplied.

The fluorescent microscope may further includes: a third optical module including: a third light source provided adjacent to the survey object to be spaced apart from the first light source and the second light source such that a bright field image of the survey object is surveyed through the first image acquisition unit and the second image acquisition unit.

The first light source may be a blue solid state fluorescence light source, the second light source may be any one of a green solid state fluorescence light source and a red solid state fluorescence light source, and the third light source may be any one of a white solid state fluorescence light source and a red solid state fluorescence light source.

The excitation filter and the second dichroic filter may correspond to dual band pass filters, respectively.

The first image acquisition unit and the second image acquisition unit may correspond to a charge-coupled device (CCD) image sensor or a complementary metal oxide semiconductor (CMOS) image sensor, respectively.

The first image acquisition unit and the second image acquisition unit may independently adjust an exposure time and a fluorescence intensity of a fluorescent image in response to the fluorescent image to be surveyed, respectively.

In accordance with still another aspect of the present invention, there is provided A fluorescent microscope for observing multiple fluorescent images, the fluorescent microscope including: a first optical module including a first light source for supplying first excitation light having a first wavelength, a first dichroic filter for reflecting the first excitation light supplied from the first light source, an excitation filter for selectively transmitting the first excitation light reflected by the first dichroic filter, a second dichroic filter for reflecting the first excitation light having passed through the excitation filter toward the survey object, an objective lens for condensing the first excitation light reflected by the second dichroic filter and transferring the condensed first excitation light to the survey object, a radiation filter for selectively transmitting first radiation light reflected by the survey object and passing through the second dichroic filter, and an image acquisition unit for acquiring an image by using the first radiation light having passed through the radiation filter to be supplied; and a second optical module including a second light source disposed adjacent to the first light source to supply second excitation light having a second wavelength in a direction crossing a progress direction of the first excitation light, the radiation filter for selectively transmitting second radiation light passing through the first dichroic filter and the excitation filter, reflected by the second dichroic filter, passing through the objective lens, irradiated to the survey object to be radiated, and passing through the second dichroic filter, and the image acquisition unit for acquiring an image by using the second radiation light having passed through the radiation filter to be supplied.

The fluorescent microscope may further include: a third light source disposed adjacent to the survey object to be spaced apart from the first light source and the second light source such that a bright field image of the survey object is surveyed through the image acquisition unit.

The first light source may be a blue solid state fluorescence light source, the second light source may be any one of a green solid state fluorescence light source and a red solid state fluorescence light source, and the third light source may be any one of a white solid state fluorescence light source and a red solid state fluorescence light source.

The excitation filter, the second dichroic filter, and the radiation filter may correspond to dual band pass filters, respectively.

In accordance with yet another aspect of the present invention, there is provided a fluorescent microscope for observing multiple fluorescent images, the fluorescent microscope including: a plurality of light sources for irradiating excitation light having different wavelengths to a survey object, respectively; a plurality of dichroic filters disposed to be spaced apart from each other, to reflect only light having a wavelength in a selected range of the radiation light radiated from the survey object, respectively; and a plurality of image acquisition units disposed to be spaced apart from each other, to acquire an image by using the reflection light reflected from the dichroic filters, respectively without a mechanical movement.

The fluorescent microscope may further include: an image processing unit for setting coordinate values of images acquired through the image acquisition units, comparing the images to detect a coordinate of the same object, calculating coordinate errors of other images with reference to a reference image to correct the coordinate values for the images, setting effective areas of the images by using the corrected coordinate values, and adjusting the images to an image on the effective area according to the set effective area to correct the images, respectively.

The dichroic filters may be disposed such that a dichroic filter reflecting radiation light having a relatively short wavelength is closer to the light source.

The fluorescent microscope may further include: a dichroic filter for, when a plurality of images are acquired by using the plurality of light sources, uniformly adjusting brightness of the images or adjusting paths of the plurality of light sources.

The light source may supply the excitation light such that the excitation light is inclined at a predetermined angle with respect to the survey object, and the fluorescent microscope may further include: a bright field light source provided at a central portion of the light source to supply white light to the survey object such that a bright field image of the survey object is surveyed through the image acquisition unit.

The fluorescent microscope may further include: a plurality of excitation filters provided between the light sources and the survey object, respectively, to selectively transmit the excitation light, respectively.

The fluorescent microscope may further include: a plurality of radiation filters provided between the dichoic filters and the image acquisition units, respectively, to selectively transmit only reflection light having a specific wavelength of the reflection light reflected from the dichroic filters.

The image acquisition units may correspond to a charge-coupled device (CCD) image sensor or a complementary metal oxide semiconductor (CMOS) image sensor, respectively.

The plurality of image acquisition units may independently adjust an exposure time and a fluorescence intensity of a fluorescent image in response to the fluorescent image to be surveyed, respectively.

In accordance with a further aspect of the present invention, there is provided a method of surveying a fluorescent image using a fluorescent microscope for observing multiple fluorescent images, the method including: acquiring images of a survey object by using excitation light having different wavelengths irradiated through a plurality of light sources; comparing outskirt areas of a first image and a second image of the acquired images, and extracting a direction of a vector; and correcting the second image with reference to the first image, considering the direction of the vector.

In accordance with a still further aspect of the present invention, there is provided a method of surveying a fluorescent image using a fluorescent microscope for observing multiple fluorescent images, the method including: acquiring images of a survey object, respectively, by using excitation light having different wavelengths irradiated through a plurality of light sources; extracting a first center area image forming a central portion of a first image of the acquired images; extracting a second center area image forming a central portion of a second image of the acquired images; comparing the first center area image and the second center area image to extract X and Y displacement values of the second center area image with respect to the first center area image; and displacing the second image by using the X and Y displacement values to correct the second image.

In accordance with a yet further aspect of the present invention, there is provided a system for observing multiple fluorescent images including: a plurality of light sources for irradiating excitation light having different wavelengths to a survey object, respectively; a plurality of dichroic filters disposed to be spaced apart from each other, to reflect only light having a wavelength in a selected range of the radiation light radiated from the survey object, respectively; a plurality of image acquisition units disposed to be spaced apart from each other, to acquire an image by using the reflection light reflected from the dichroic filters, respectively without a mechanical movement; and an image processing unit for processing a plurality of images acquired through the plurality of image acquisition units such that the images are compared with each other, and the image processing unit corrects the plurality of images through the steps of: acquiring images of a survey object by using excitation light having different wavelengths irradiated through a plurality of light sources; comparing outskirt areas of a first image and a second image of the acquired images, and extracting a direction of a vector; and correcting the second image with reference to the first image, considering the direction of the vector.

Advantageous Effects

According to the present invention, the fluorescent microscope for observing multiple fluorescent images includes a plurality of image acquisition units corresponding to the number of light sources from which light is irradiated, whereby a plurality of fluorescent images can be simply and promptly observed without a mechanical movement.

MODE FOR CARRYING OUT THE INVENTION

Hereinafter, exemplary embodiments of the present invention will be described in detail with reference to the accompanying drawings. In the description of the present invention, known functions and configurations will not be described to make the essence of the present invention clear.

Figure 1:
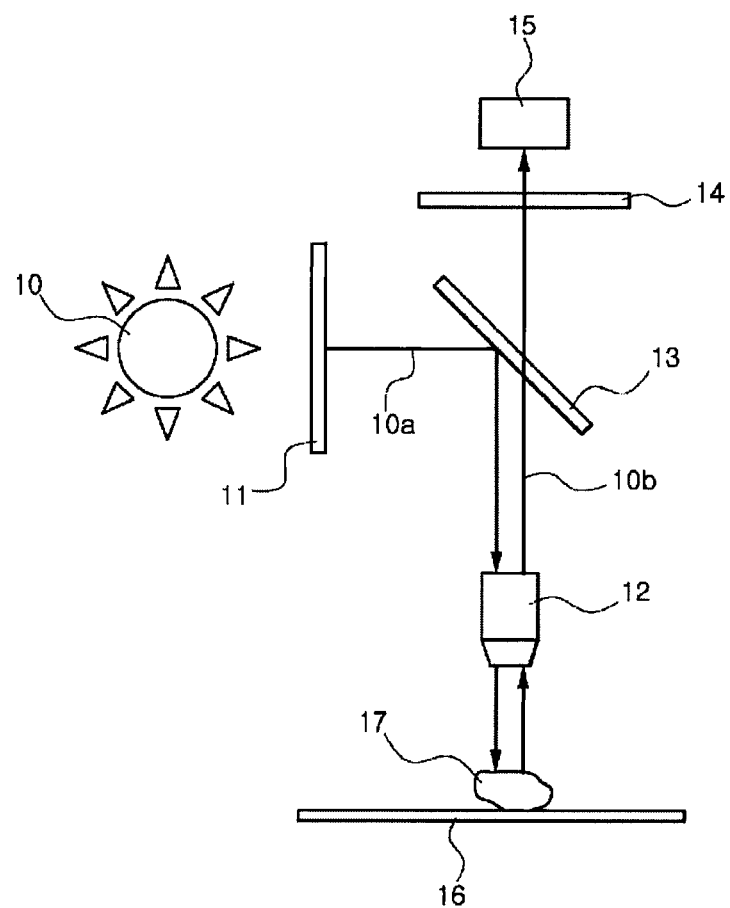
FIG. 1 is a schematic diagram illustrating a general fluorescent microscope according to the related art.
Figure 2:
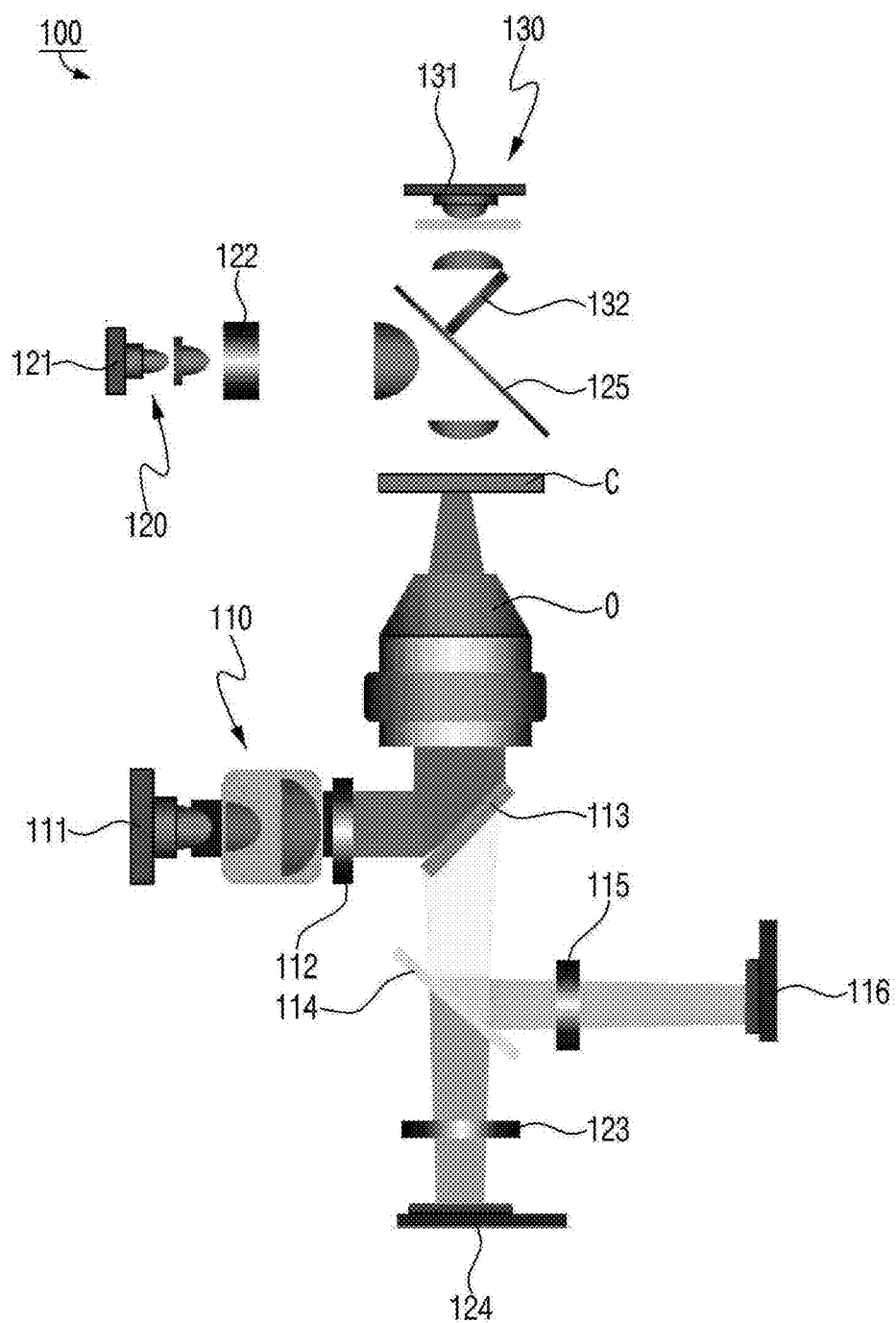
FIG. 2 is a schematic diagram illustrating a fluorescent microscope according to the first embodiment of the present invention.
Figure 3:
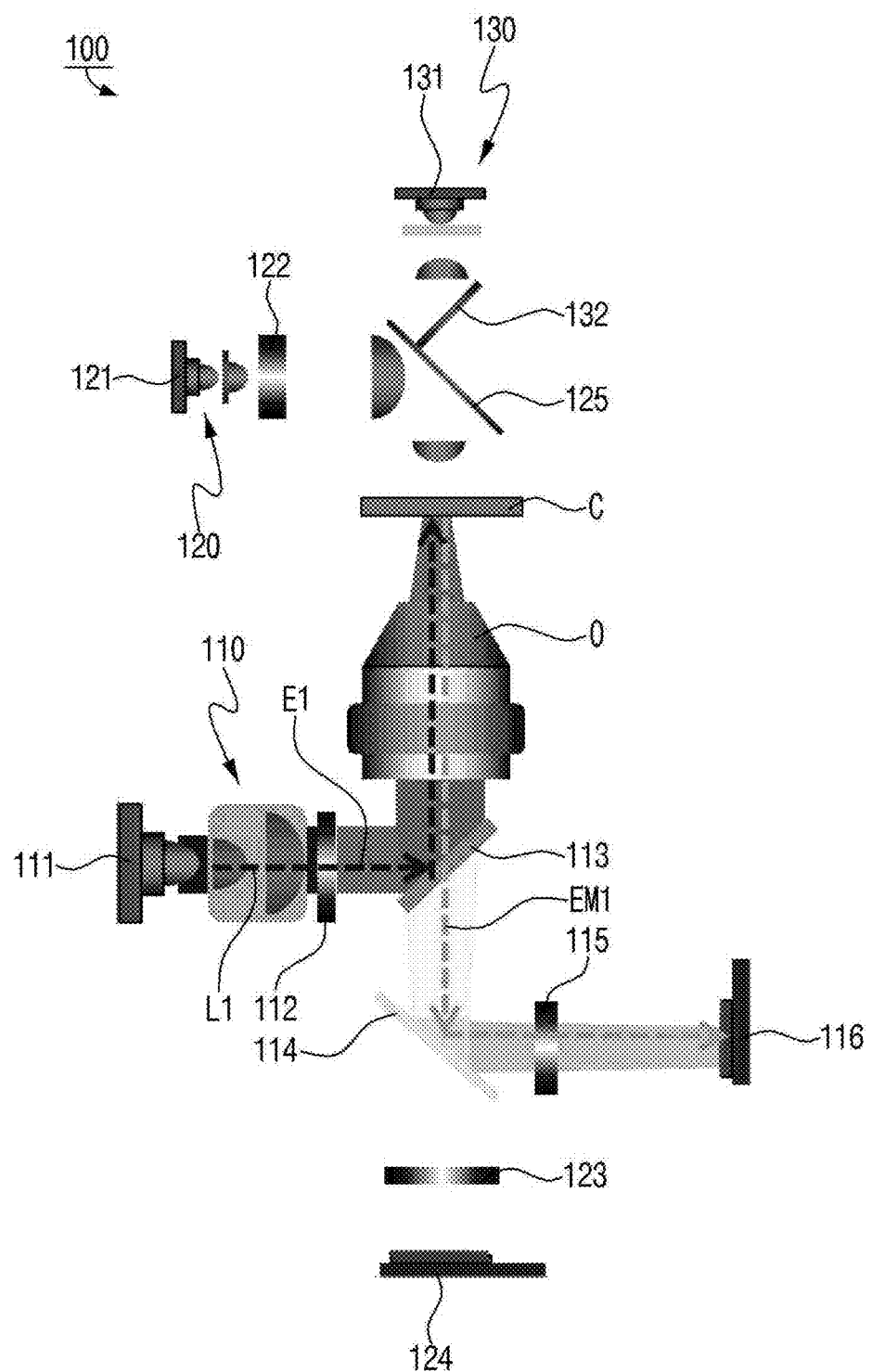
FIG. 3 is a schematic diagram illustrating a principle of acquiring an image of a survey object with a first optical module of the fluorescent microscope of FIG. 2.
Figure 4:
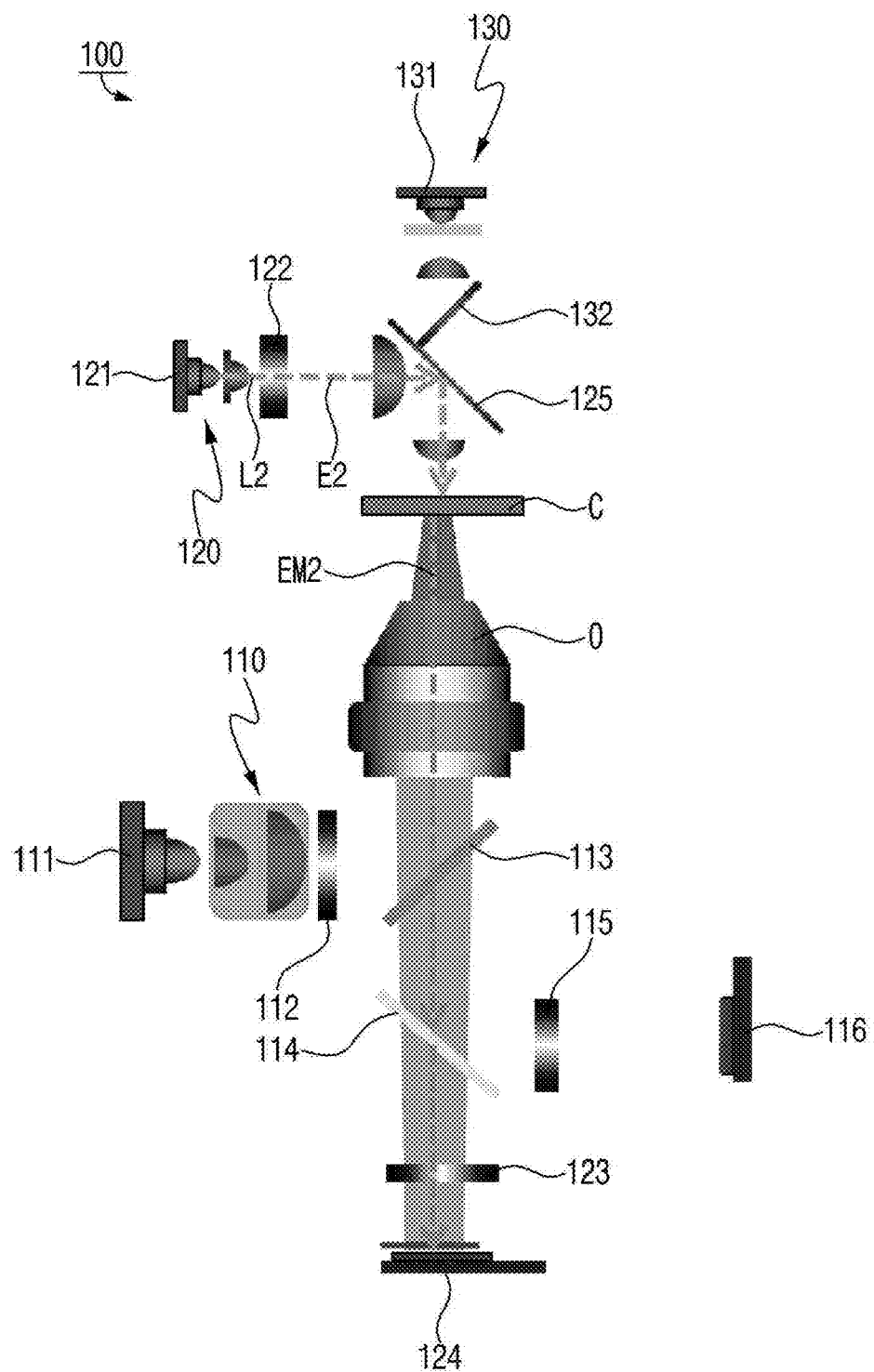
FIG. 4 is a schematic diagram illustrating a principle of acquiring an image of a survey object with a second optical module of the fluorescent microscope of FIG. 2.
Figure 5:
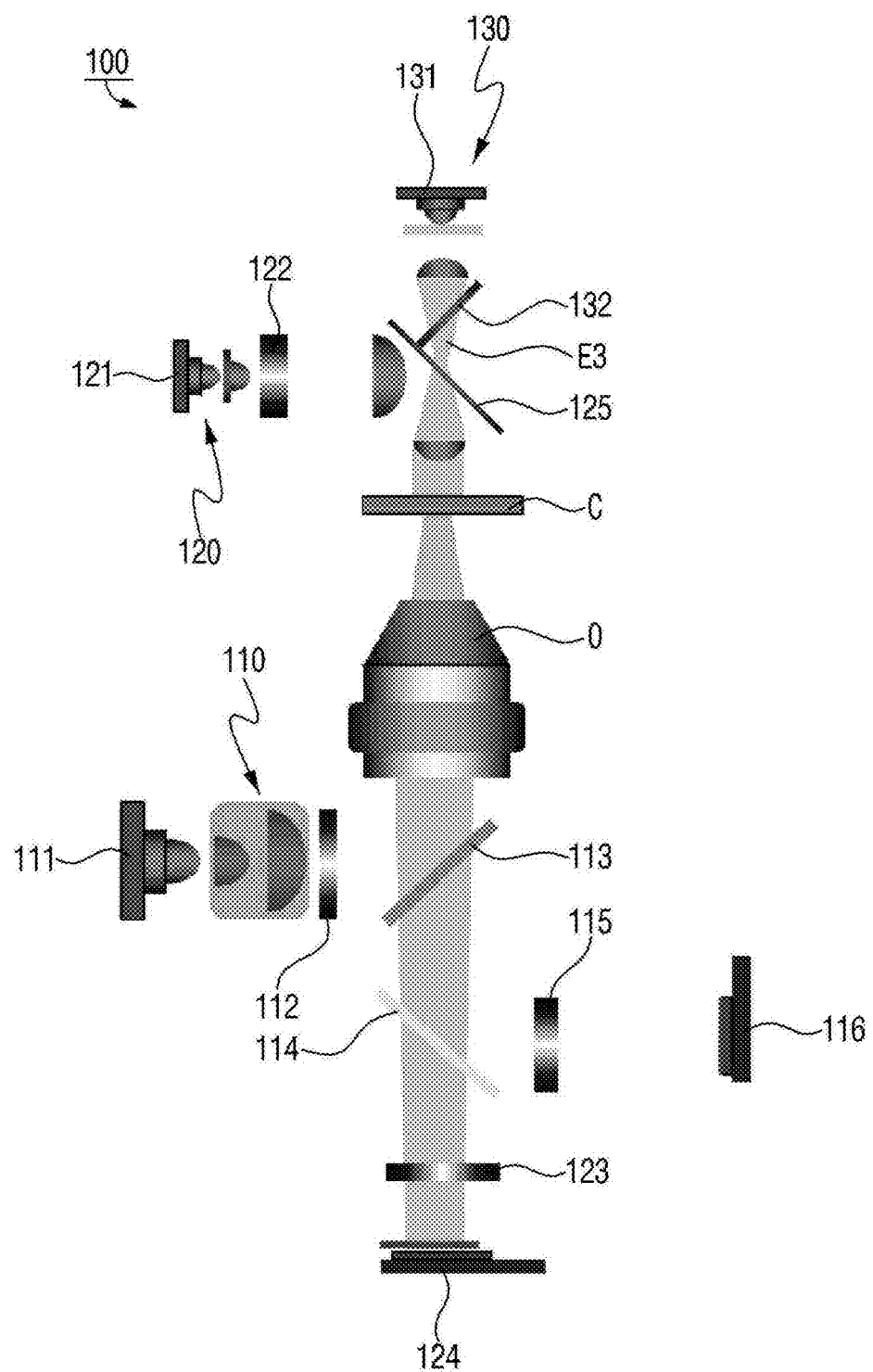
FIG. 5 is a schematic diagram illustrating a principle of acquiring an image of a survey object with a third optical module of the fluorescent microscope of FIG. 2.

FIG. 2 is a schematic diagram illustrating a fluorescent microscope according to the first embodiment of the present invention. FIG. 3 is a schematic diagram illustrating a principle of acquiring an image of a survey object with a first optical module of the fluorescent microscope of FIG. 2. FIG. 4 is a schematic diagram illustrating a principle of acquiring an image of a survey object with a second optical module of the fluorescent microscope of FIG. 2. FIG. 5 is a schematic diagram illustrating a principle of acquiring an image of a survey object with a third optical module of the fluorescent microscope of FIG. 2.

Hereinafter, a survey object refers to an object-to-be-surveyed processed through a fluorescent sample, for example, a biochip.

Referring to the drawings, the fluorescent microscope 100 according to the first embodiment of the present invention includes a first optical module 110 for acquiring an image of a survey object C by using a first light source 111, a second optical module 120 for acquiring an image of the survey object C by using a second light source 121, and a third optical module 130 provided to obtain a bright field image of the survey object C.

The first optical module 110 is configured to acquire a fluorescent image of the survey object C by using the first light source 111, and includes a first light source 111 for supplying first excitation light L1, a first excitation filter 112 for selectively transmitting the first excitation light L1 supplied from the first light source 111, a first dichroic filter 113 for reflecting the first excitation light E1 having passed through the first excitation filter 112 toward the survey object C, an objective lens O for condensing the first excitation light E1 and transferring the condensed first excitation light E1 to the survey object C, a second dichroic filter 114 for reflecting first radiation light EM1 radiated from the survey object C by the first excitation light E1, a first radiation filter 115 for selectively transmitting the first radiation light EM1 reflected by the second dichroic filter 114, and a first image acquisition unit 116 for acquiring an image by using the first radiation light EM1 having passed through the first radiation filter 115 to be supplied.

Here, the first excitation light L1 supplied by the first light source 111, the first excitation light E1 having passed through the first excitation filter 112, and the first radiation light EM1 radiated from the survey object C are denoted by different reference symbols, considering the differences of the wavelengths of the light, and the items are the same in the exemplary embodiments of the present invention, and thus will not be repeatedly described.

The first light source 111 is configured to supply the first excitation light L1 having a first wavelength W1, and in the present embodiment, a blue solid state fluorescence light source, in particular, a light emitting diode (LED) is used. The first light source 111, that is, an LED has a long life span as compared with a general mercury or Xenon arc type lamp, reducing the frequency of maintenance operations for replacing the first light source 111, deteriorates an amount of light less in proportion to a lighting time, allowing the first image acquisition unit 116 to obtain a stable image of the survey object C, emits a small amount of heat, preventing thermal deformation of the survey object C, and has a small-sized LED, miniaturizing the fluorescent microscope 100. Of course, according to other embodiments of the present invention, a general mercury lamp may be used as the first light source 111 or a solid state fluorescence light source other than an LED may be used.

The first excitation filter 112 is configured to selectively transmit the first excitation light L1 supplied from the first light source 111, and the first dichroic filter 113 is provided adjacent to the first excitation filter 112 to reflect the first excitation light E1 transferred from the first excitation filter 112 toward the survey object C.

Generally, a dichroic filter functions to reflect light having a short wavelength and pass light having a long wavelength, and the first dichroic filter 113 of the present embodiment reflects the first excitation light E1 toward the survey object C or passes the first radiation light EM1 having a wavelength longer than that of the first excitation light E1 radiated from the survey object C as it is, allowing the first image acquisition unit 116 to acquire an image of the survey object C.

The objective lens O is configured to condense the first excitation light E1 reflected by the first dichroic filter 113 and transfer the condensed first excitation light E1 to the survey object C. The first excitation light E1 reflected by the first dichroic filter 113 is condensed by the objective lens O and then is irradiated to the survey object to convert energy of the survey object C into a temporarily excited state, and the survey object C emits the absorbed energy again and returns to a stable state while emitting fluorescent light. Hereinafter, the fluorescent light generated from the survey object C by the first excitation light E1 is referred to as first radiation light EM1.

As known in the art, the first radiation light E1 has a wavelength slightly displaced toward the red as compared with the first excitation light E1, and the change is called a stokes shift. That is, the first radiation light EM1 has a wavelength slightly longer than the first excitation light E1 according to the stokes shift, and the survey object C provided with the first excitation light E1 by the first light source 111, that is, a blue LED as in the present embodiment radiates light having a wavelength longer than that of blue light, for example, the first radiation light EM1 of a green color.

The first radiation light EM1 radiated from the survey object C is reflected by the second dichroic filter 114 after passing through the objective lens O and the first dichroic filter 113 so that a path thereof is changed toward the first image acquisition unit 116. As described above, the first dichroic filter 113 functions to reflect the first excitation light E1 having a wavelength shorter than that of the first radiation light EM1 toward the survey object C but pass the first radiation light EM1 having a wavelength longer than that of the first excitation light E1 as it is.

The second dichroic filter 114 functions to reflect the first radiation light EM1 radiated from the survey object C toward the first image acquisition unit 116, and the first radiation filter 115 is provided between the second dichroic filter 114 and the first image acquisition unit 116 to selectively transmit the first radiation light EM1 reflected by the second dichroic filter 114 and then transfer the first radiation light EM1 to the first image acquisition unit 116.

That is, since a kind of optical noise is mixed in the first radiation light EM1 radiated from the survey object C and reflected by the second dichroic filter 114, the first radiation filter 115 removes such optical noise and transfers only the first radiation light EM1 having a desired wavelength to the first image acquisition unit 116 to help the first acquisition unit 116 to obtain a clear image.

The first image acquisition unit 116 is configured to visually realize an image of the survey object C through the first radiation light EM1 having passed through the first radiation filter 115 to be provided. The first image acquisition unit 116 of the present embodiment is a charge-coupled device (CCD) image sensor or a complementary metal oxide semiconductor (CMOS) image sensor.

Here, the CCD image sensor refers to an image sensor of the type in which after a CCD is exposed to light, information is copied to readout registers one by one from the lowermost row to read out charges stored in photosites, and the copied values are converted into numbers through an amplifier and an analogue-to-digital converter again, so that the registers are sequentially read out from the lowermost row to the uppermost row.

Further, the CMOS image sensor refers to a solid state image pickup device which uses a photo diode like the CCD image sensor but uses a complimentary metal oxide semiconductor, which is manufactured and reads out signals in different ways.

The first image acquisition unit 116 of the present embodiment may use any one of a CCD image sensor and a CMOS image sensor, but preferably uses a CMOS image sensor, considering improvement of integration, power consumptions and the like. Meanwhile, since it may be more preferable to use a CCD image sensor, considering a noise level, noise processing, and an image quality, a suitable image sensor needs to be adopted, considering a required specification of the fluorescent microscope 100.

The first image acquisition unit 116 may obtain a green fluorescent protein (GFP) image of the survey object C by using the first light source 111.

Meanwhile, a second optical module 120 is configured to acquire an image of a survey object C by using a second light source 121, and includes a second light source 121 for supplying second excitation light L2, a second excitation filter 122 for selectively transmitting the second excitation light L2 supplied from the second light source 121, a second radiation filter 123 for selectively transmitting the second radiation light EM2 having passed through the second excitation filter 122 and irradiated to the survey object C to be radiated, and a second image acquisition unit 124 for acquiring an image by using the second radiation light EM2 having passed through the second radiation filter 123 to be supplied.

The second light source 121 is configured to supply the second excitation light L2 having a second wavelength W2, and is a green LED in the present embodiment. Of course, as described above, the second light source 121 may be a general mercury lamp. Further, since it will do good as long as the second light source 121 supplies the second excitation light L2 having a wavelength shorter than that of the first light source 111, the second light source 121 is a red LED when the first light source 111 is a greed LED (the items are the same in the second and third embodiments).

The second excitation filter 122 is configured to selectively transmit the second excitation light L2 supplied from the second light source 121. The second excitation light E2 having passed through the second excitation filter 122 to be transferred to the survey object C converts energy of the survey object C into a temporarily excited state, and the survey object C emits the absorbed energy again and returns to a stable state while emitting fluorescent light. Hereinafter, the fluorescent light generated from the survey object C by the second excitation light E2 is referred to as second radiation light EM2.

Similar to the case of the above-described first optical module 110, the second radiation light E2 has a wavelength slightly longer than the second excitation light E2 according to the stokes shift, and the survey object C provided with the second excitation light E2 by the second light source 121, that is, a green LED as in the present embodiment radiates light having a wavelength longer than that of green light, for example, the second radiation light EM2 of a red color.

After the second radiation light EM2 radiated from the survey object C passes through the objective lens O, the first dichroic filter 113, and the second dichroic filter 114, only the second radiation light EM2 from which optical noise is removed by the second radiation filter 123 is transferred to the second image acquisition unit 124.

Like the first image acquisition unit 116, the second image acquisition unit 124 is a CCD image sensor or a CMOS image sensor, and acquires a red fluorescent protein (RFP) image of the survey object C through the second radiation light EM2 having passed through the second radiation filter 123 to be transferred.

Meanwhile, the first image acquisition unit 116 and the second image acquisition unit 124 of the present embodiment can adjust exposure time and intensity of fluorescent light in response to the GFP image or RFP image to be surveyed. Generally, a fluorescent microscope includes only one survey part corresponding to the image acquisition unit 115 or 124 of the present embodiment, and should continuously adjust exposure time of a fluorescent image or intensity of fluorescent light to survey an RFP image after surveying a GFP image or survey a GFP image after surveying an RFP image. That is, the fluorescent microscope according to the related art surveys a signal with one surveying part and thus various kinds of fluorescent light are sequentially viewed while individual conditions are continuously adjusted in the form of a turret or a revolver, whereas the fluorescent microscope 100 of the present embodiment includes the first image acquisition unit 116 and the second image acquisition unit 124 which can be adjusted independently, and thus an image can be continuously surveyed while a survey condition of a GFP image or a survey condition of an RFP image is individually adjusted. The items are the same in the other embodiment of the present invention, and a description thereof will not be repeated.

Meanwhile, some of the second excitation light E2 irradiated to the survey object C passes through the survey object C as it is to be transferred, and the second excitation light E2 having passed through the survey object C to be transferred is reflected by the second dichroic filter 114 after passing through the first dichroic filter 113, and is transferred to the first image acquisition unit 116 while optical noise is removed by the first radiation filter 115. The first image acquisition unit 116 may obtain a bright field image of the survey object C through the second excitation light E2. That is, the second image acquisition unit 124 obtains an RFP image with the second light source 121, and the first image acquisition unit 116 obtains a bright field image.

As illustrated in FIG. 2, in the present embodiment, since the second light source 121 supplies the second excitation light L2 in a direction parallel to the survey object C, a configuration for converting the second excitation light L2 to the survey object C is necessary, and this a third dichroic filter 125 in charge of such a role is additionally provided.

The third optical module 130 is configured to obtain a bright field image of a survey object C by using a third light source 131, and includes a third light source 131 for supplying third excitation light L3, and a fourth dichroic filter 132 disposed in a direction perpendicular to a disposition direction of the third dichroic filter 125.

The third light source 131 is a white and irradiates white light to the survey object C. The white light irradiated to the survey object C moves forward to the second image acquisition unit 124 as it is, and a surveyor can survey a bright field image of the survey object C through the second image acquisition unit 124. The bright field image acquired by the third light source is the same as that of a general optical microscope, and will not be described in detail.

The fourth dichroic filter 132 is disposed in a direction perpendicular to a disposition direction of the third dichroic filter 125 so that a brightness of the bright field image acquired by the second image acquisition unit 124 can be uniformly adjusted.

The brightness of the bright field image acquired through the second image acquisition unit 124 may not be uniform if only the third dichroic filter 125 is used, so the brightness of the bright field image acquired by the second acquisition unit 124 may be adjusted uniformly by disposing a pair of dichroic filters 125 and 132 such that the dichroic filters 125 and 132 are perpendicular to each other.

Meanwhile, as described above, the fluorescent microscope 100 of the present embodiment is devised to obtain a bright field image even through the second light source 120, and thus the third module 130 may be omitted if necessary.

The fluorescent microscope 100 of the present invention includes the first image acquisition unit 116 and the second image acquisition unit 124, and thus simply and promptly surveys a plurality of fluorescent images without a mechanical movement.

Figure 6:
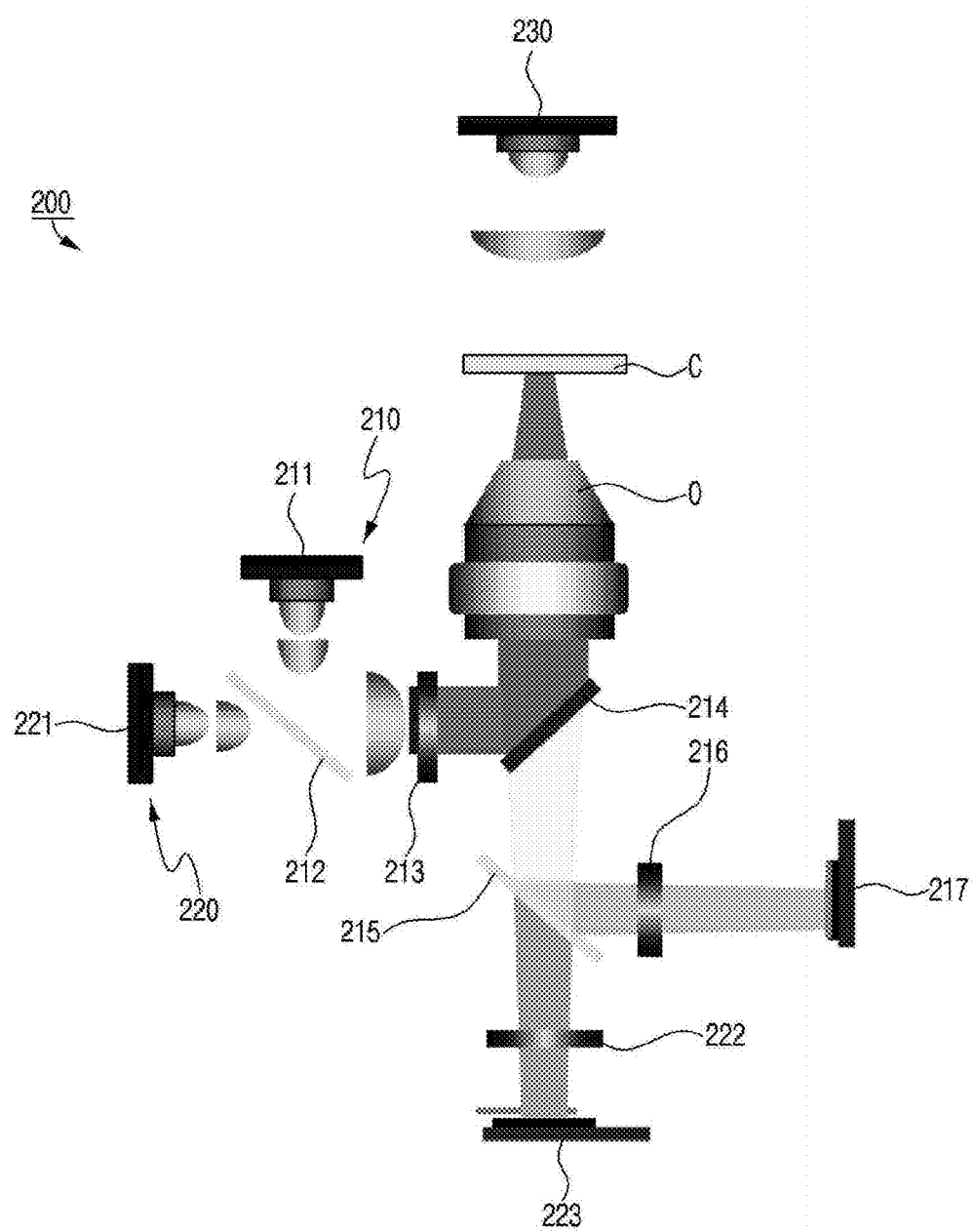
FIG. 6 is a schematic diagram illustrating a fluorescent microscope according to the second embodiment of the present invention.
Figure 7:
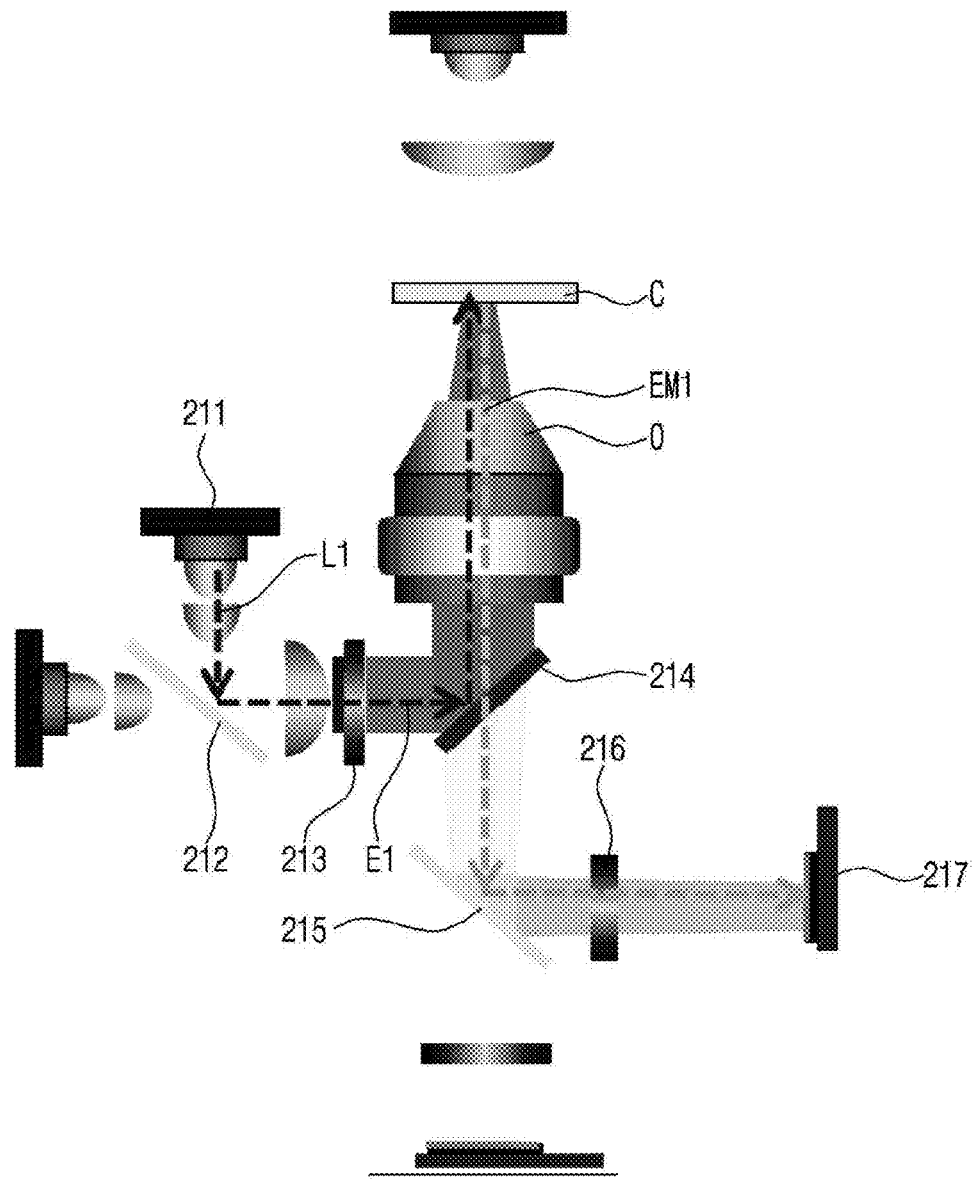
FIG. 7 is a schematic diagram illustrating a principle of acquiring an image of a survey object with a first optical module of the fluorescent microscope of FIG. 6.
Figure 8:
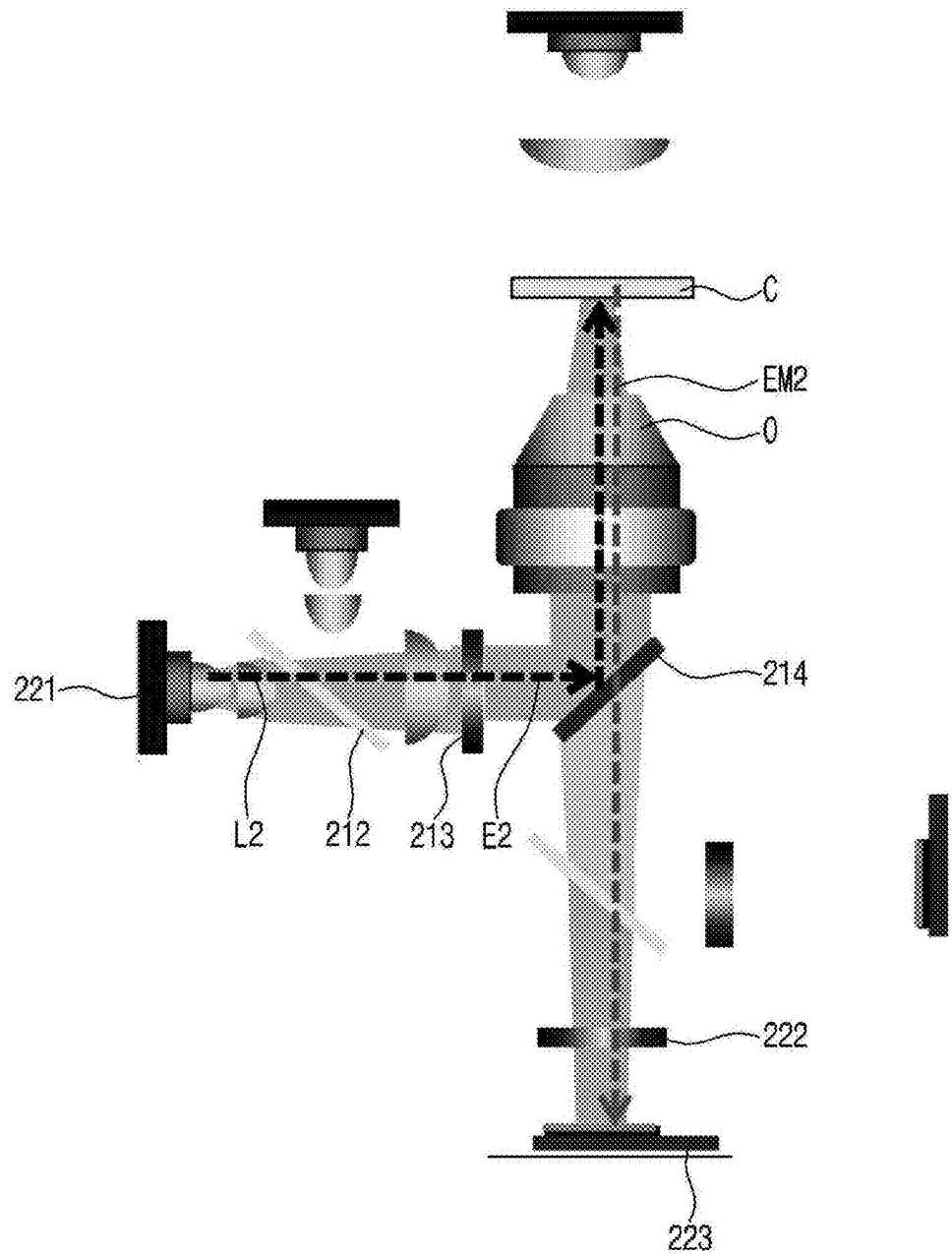
FIG. 8 is a schematic diagram illustrating a principle of acquiring an image of a survey object with a second optical module of the fluorescent microscope of FIG. 6.
Figure 9:
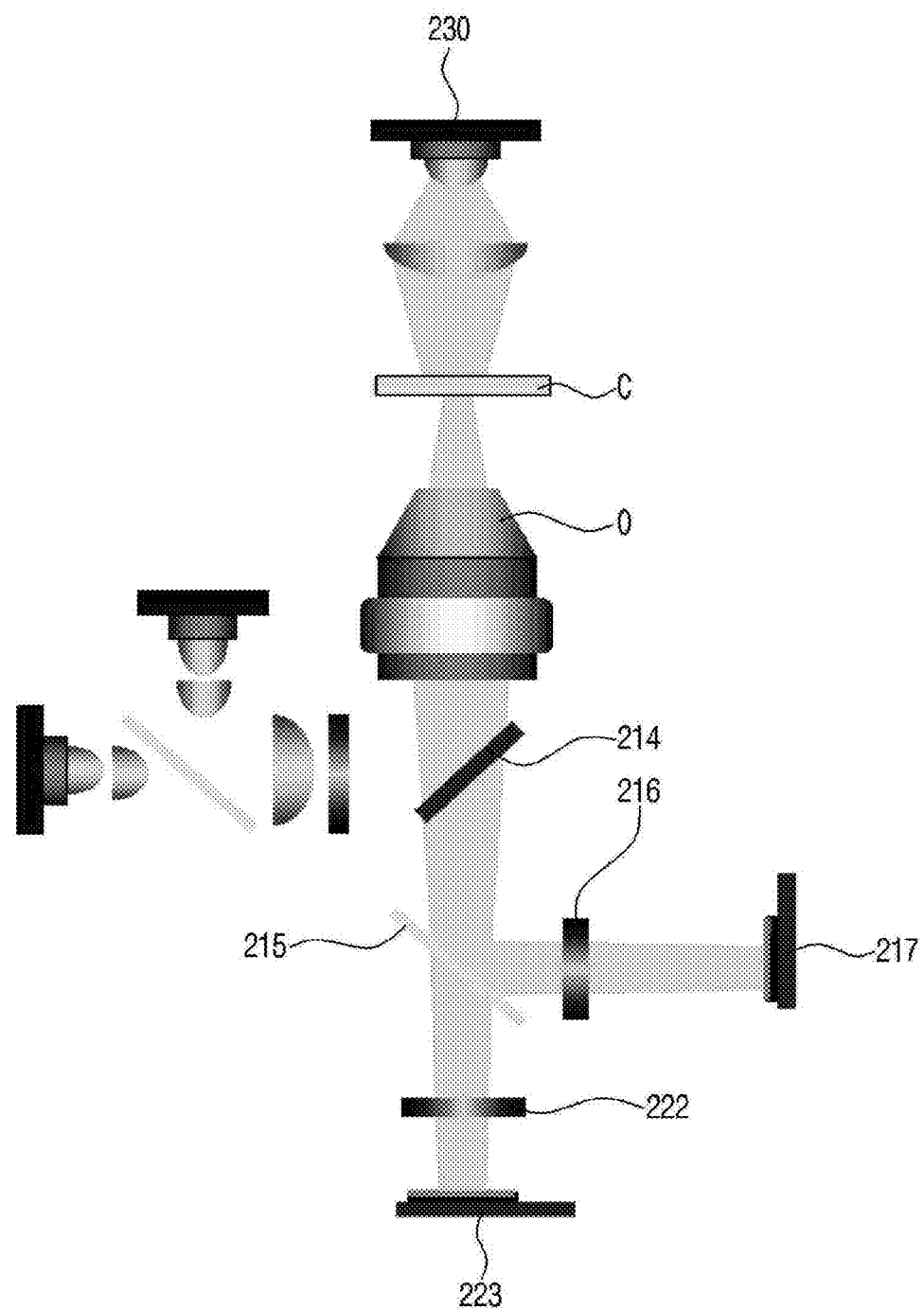
FIG. 9 is a schematic diagram illustrating a principle of acquiring an image of a survey object by using a third optical light source of the fluorescent microscope of FIG. 2.

FIG. 6 is a schematic diagram illustrating a fluorescent microscope according to the second embodiment of the present invention. FIG. 7 is a schematic diagram illustrating a principle of acquiring an image of a survey object with a first optical module of the fluorescent microscope of FIG. 6. FIG. 8 is a schematic diagram illustrating a principle of acquiring an image of a survey object with a second optical module of the fluorescent microscope of FIG. 6. FIG. 9 is a schematic diagram illustrating a principle of acquiring an image of a survey object by using a third optical light source of the fluorescent microscope of FIG. 6.

Referring to the drawings, the fluorescent microscope 200 according to the second embodiment of the present invention includes a first optical module 210 for acquiring an image of a survey object C by using a first light source 211, a second optical module 220 for acquiring an image of the survey object C by using a second light source 221, and a third optical module 230 provided to obtain a bright field image of the survey object C.

The first optical module 210 is configured to acquire a fluorescent image of the survey object C by using the first light source 211, and includes a first light source 211 for supplying first excitation light L1 having a first wavelength W1, a first dichroic filter 212 for reflecting the first excitation light L1 supplied from the first light source 211, an excitation filter 213 for selectively transmitting the first excitation light L1 supplied from the first dichroic filter 212, a second dichroic filter 214 for reflecting the first excitation light E1 having passed through the first excitation filter 213 toward the survey object C, an objective lens O for condensing the first excitation light L1 reflected by the second dichroic filter 214 and transferring the condensed first excitation light L1 to the survey object C, a third dichroic filter 215 for reflecting first radiation light EM1 radiated from the survey object C, a first radiation filter 216 for selectively transmitting the first radiation light EM1 reflected by the third dichroic filter 215, and a first image acquisition unit 217 for acquiring an image of the survey object C by using the first radiation light EM1 having passed through the first radiation filter 216 to be supplied.

A second optical module 220 is configured to acquire a fluorescent image of a survey object C by using a second light source 221, and includes a second light source 221 for supplying second excitation light L2 having a second wavelength W2, a second radiation filter 222 for selectively transmitting the second radiation light EM2 having a wavelength substantially the same as that of the second radiation light EM2 having passed through the excitation filter 213 to be reflected by the second dichroic filter 214 and having passed through the objective lens O and irradiated to the survey object C to be radiated, and a second image acquisition unit 223 for acquiring an image by using the second radiation light EM2.

Here, the items regarding the first light source 211, the third dichroic filter 215, the first radiation filter 216, the first image acquisition unit 217, the second light source 221, the second radiation filter 222, the second image acquisition unit 223, and the third light source 230 are substantially the same as the items regarding the first light source 111, the second dichronic filter 114, the first radiation filter 115, the first image acquisition unit 116, the second light source 121, the second radiation filter 123, the second image acquisition unit 124, and the third light source of the above-described first embodiment, respectively, and thus a repeated description will be omitted.

Meanwhile, unlike the above-described first embodiment, the first light source 211 and the second light source 221 are disposed adjacent to each other in one module such that the first excitation light L1 and the second excitation light L2 are supplied in directions crossing each other, and the third light source 230 is provided separately from the first light source 211 and the second light source 221. When a fluorescent image is to be obtained according to the configuration, the first light source 211 and the second light source 221 are sequentially adjusted, whereas when a bright field image of the survey object C is to be obtained, only the third light source 230 may be used to simply obtain the bright field image.

The first dichroic filter 212 is provided adjacent to the first light source 211 to reflect the first excitation light L1 supplied from the first light source 211 toward the excitation filter 213, and the excitation filter 213 selectively transmits the first excitation light L1 reflected by the first dichroic filter 212.

In particular, in the present embodiment, the excitation filter 213 is a dual band pass filter to pass only two kinds of light having different wavelengths. That is, the excitation filter 213 is provided to transmit both of the first excitation light L1 of the first light source 211 providing blue light and the second excitation light L2 of the second light source 221 providing green light.

Likewise, the second dichroic filter 214 of the present invention is a dual band pass filter to pass both of the first radiation light EM1 which is green light radiated from the survey object C by the first light source 211 and the second radiation light EM2 which is red light radiated from the survey object C by the second light source 221.

A process of acquiring a fluorescent image or a bright field image of a survey object C by using the fluorescent microscope 200 of the present embodiment is as follows.

First, the surveyor turns on the first light source 211 so that blue light is irradiated from the first light source 211. After being reflected by the first dichroic filter 212, the first excitation light L1 supplied from the first light source 211 passes through the excitation filter 213, and the first excitation light E1 having passed through the excitation filter 213 is reflected by the second dichroic filter 214 and condensed through the objective lens O, and then is irradiated to the survey object C. The first radiation light EM1 which is green light is radiated from the survey object C having received the first excitation light E1 is radiated, and the first radiation light EM1 passes through the objective lens O and the second dichroic filter 214 and is reflected by the third dichroic filter 215, and a fluorescent image (GFP) is obtained through the first image acquisition unit 217 after optical noise is removed by the first radiation filter 216.

Next, the surveyor turns off the first light source 211 and turns on the second light source 221 to irradiate green light from the second light source 221. After passing through the first dichroic filter 212 and the excitation filter 213, the second excitation light L2 supplied from the second light source 221 is reflected toward the survey object C by the second dichroic filter 214, and after the second radiation light EM2 emitting from the survey object C passes through the objective lens O, the second dichroic filter 214, and the third dichroic filter 215, a fluorescent image (RFP) is obtained through the second image acquisition unit 223 after optical noise is removed by the second radiation filter 222.

Finally, the surveyor turns off the second light source 221 and turns on the third light source 230 to irradiate white light from the third light source 230. After the white light supplied from the third light source 230 passes the survey object C, the objective lens O, and the second dichroic filter 214 as it is, some of the white light is reflected toward the first image acquisition unit 217 by the third dichroic filter 215, the remaining white light passes through the third dichroic filter 215 as it is and proceeds to the second image acquisition unit 223. The surveyor surveys a bright field image of the survey object C through the first image acquisition unit 217 and the second image acquisition unit 223.

Figure 10:
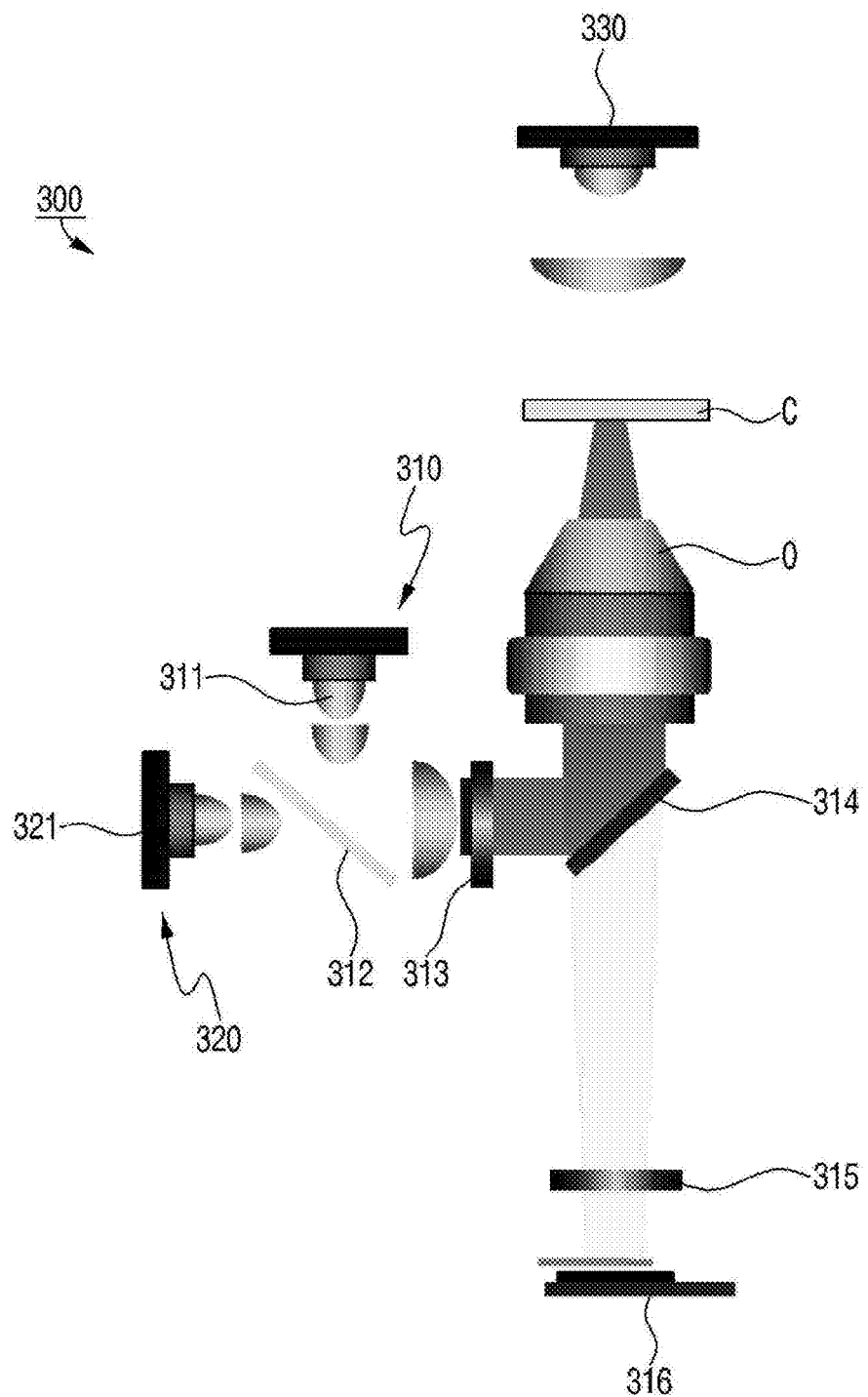
FIG. 10 is a schematic diagram illustrating a fluorescent microscope according to the third embodiment of the present invention.
Figure 11:
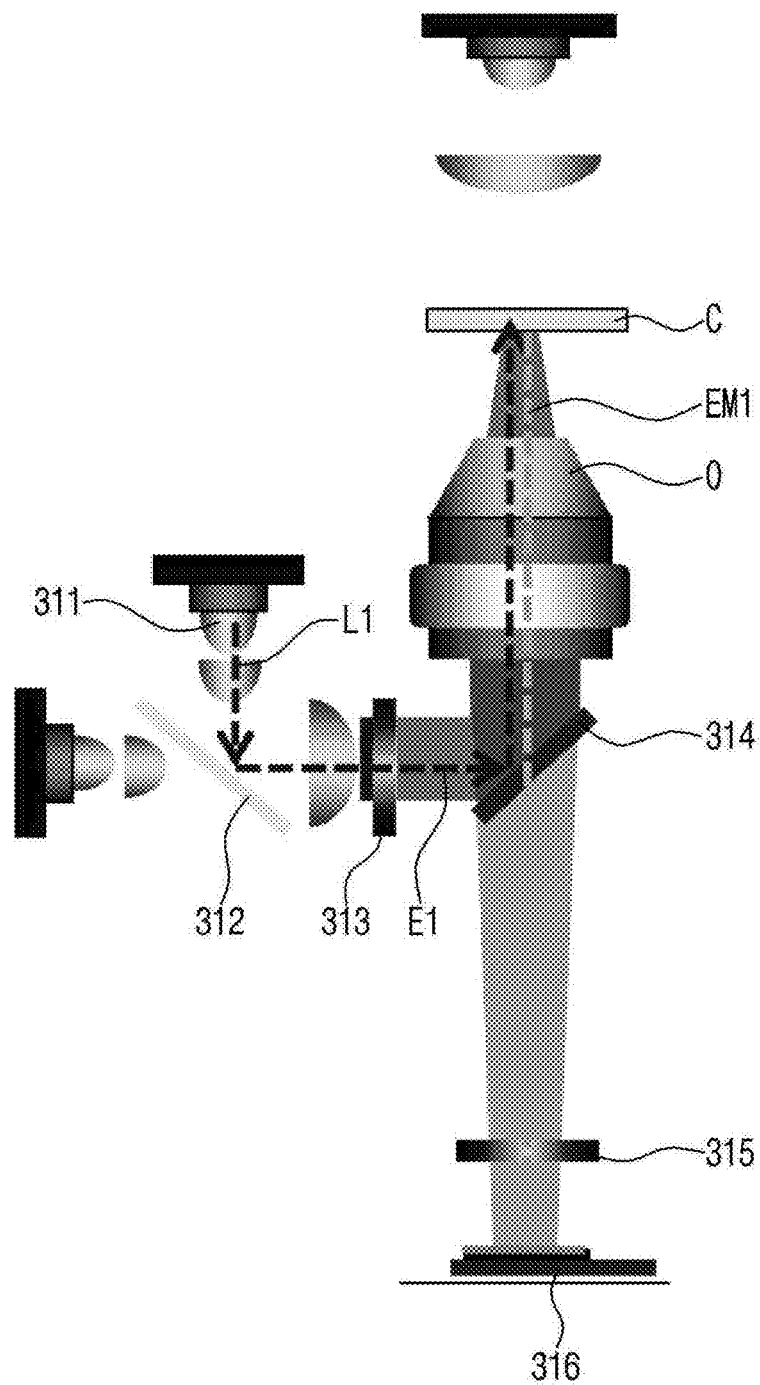
FIG. 11 is a schematic diagram illustrating a principle of acquiring an image of a survey object with a first optical module of the fluorescent microscope of FIG. 10.
Figure 12:
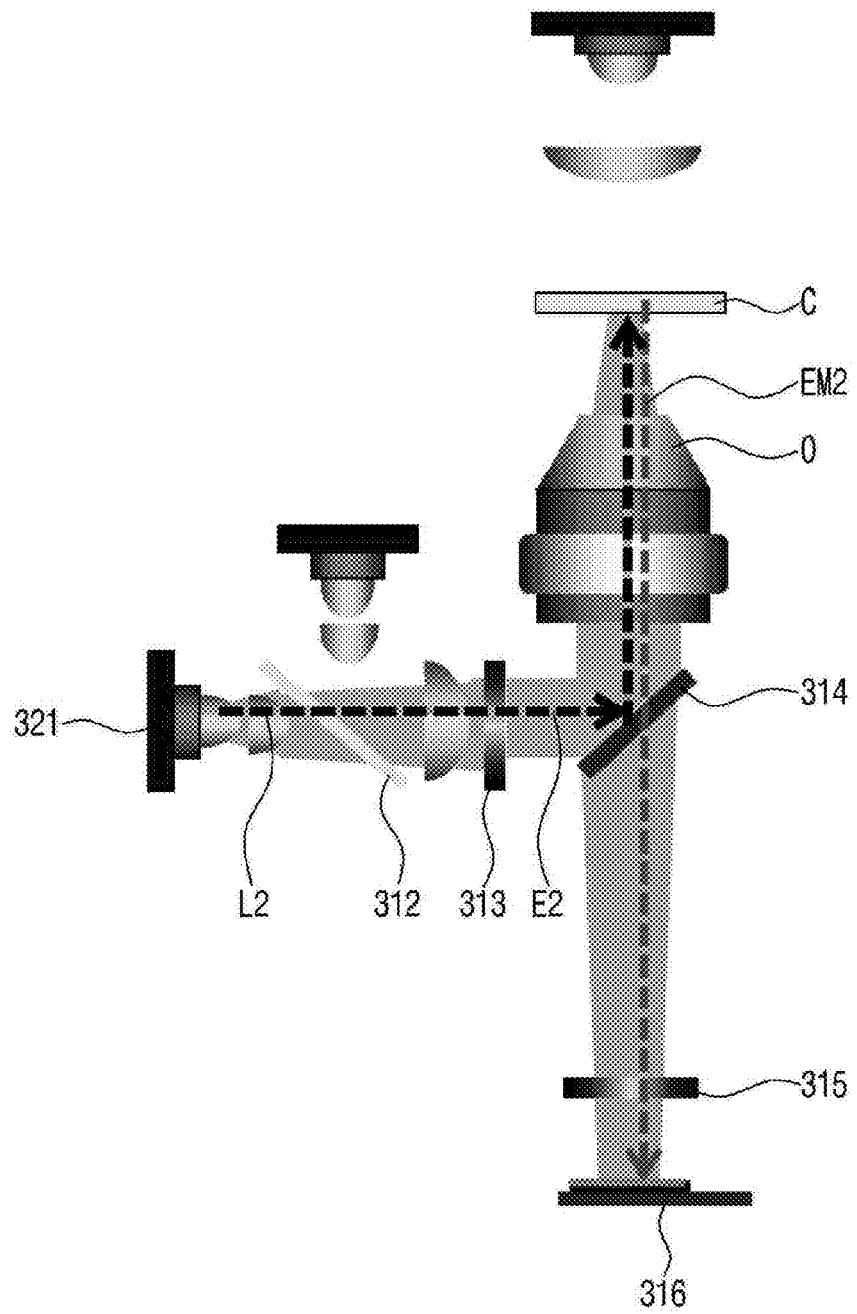
FIG. 12 is a schematic diagram illustrating a principle of acquiring an image of a survey object with a second optical module of the fluorescent microscope of FIG. 10.
Figure 13:
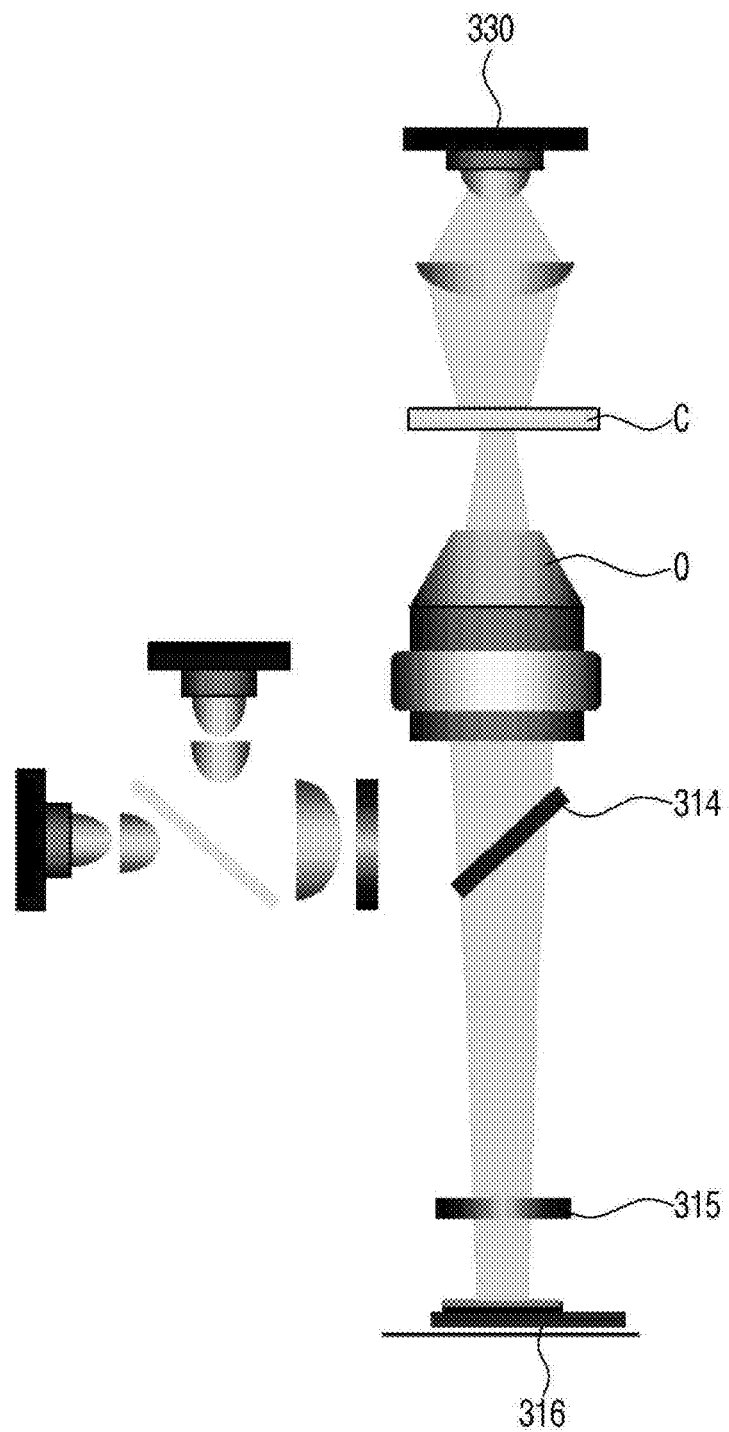
FIG. 13 is a schematic diagram illustrating a principle of acquiring an image of a survey object by using a third optical light source of the fluorescent microscope of FIG. 10.

FIG. 10 is a schematic diagram illustrating a fluorescent microscope according to the third embodiment of the present invention. FIG. 11 is a schematic diagram illustrating a principle of acquiring an image of a survey object with a first optical module of the fluorescent microscope of FIG. 10. FIG. 12 is a schematic diagram illustrating a principle of acquiring an image of a survey object with a second optical module of the fluorescent microscope of FIG. 10. FIG. 13 is a schematic diagram illustrating a principle of acquiring an image of a survey object by using a third optical light source of the fluorescent microscope of FIG. 10.

Referring to the drawings, the fluorescent microscope 300 according to the first embodiment of the present invention includes a first optical module 310 for acquiring an image of a survey object C by using a first light source 311, a second optical module 320 for acquiring an image of the survey object C by using a second light source 321, and a third light source 330 provided to obtain a bright field image of the survey object C.

The first optical module 310 is configured to acquire a fluorescent image of the survey object C by using the first light source 311, and includes a first light source 311 for supplying first excitation light L1 having a first wavelength W1, a first dichroic filter 312 for reflecting the first excitation light L1 supplied from the first light source 311, an excitation filter 313 for selectively transmitting the first excitation light L1 reflected by the first dichroic filter 312, a second dichroic filter 314 for reflecting the first excitation light E1 having passed through the excitation filter 313 toward the survey object C, an objective lens O for condensing the first excitation light L1 reflected by the second dichroic filter 314 and transferring the condensed first excitation light L1 to the survey object C, a radiation filter 315 for selectively transmitting the first radiation light EM1 radiated from the survey object C, a and an image acquisition unit 316 for acquiring an image of the survey object by using the first radiation light EM1 having passed through the first radiation filter 315 to be supplied.

Further, a second optical module 320 is configured to acquire an image of a survey object C by using a second light source 321, and includes a second light source 321 for supplying second excitation light L2 having a second wavelength W2, and a third light source 330 is provided to obtain a bright field image of the survey object C.

Here, the items regarding the first light source 311, the first dichroic filter 312, the excitation filter 313, the second dichroic filter 314, the image acquisition unit 316, the second light source 321, and the third light source 330 are substantially the same as the items regarding the first light source 211, the first dichroic filter 212, the excitation filter 213, the second dichroic filter 214, the first image acquisition unit 217, the second light source 221, and the third light source 230 of the above-described second embodiment, respectively, and thus a repeated description thereof will be omitted.

The radiation filter 315 is provided adjacent to the image acquisition unit 316 to selectively transmit the first radiation light EM1 and the second radiation light EM2. To this end, a dual band pass filter is provided as the radiation filter 315 of the present invention to remove optical noise contained in the first radiation light EM1 which is green light and the second radiation light EM2 which is red light while passing both the first radiation light EM1 and the second radiation light EM2.

That is, one dual band pass filter is provided as the radiation filter 315 to obtain both the fluorescent images (GFP and RFP) of the survey object C while removing the optical noise contained in the first radiation light EM1 and the second radiation light EM2.

The other items regarding a method of using the fluorescent microscope 300 of the present embodiment are the same as the items regarding the method of using the fluorescent microscope 200 of the second embodiment, and a repeated description thereof will be omitted.

Figure 14:
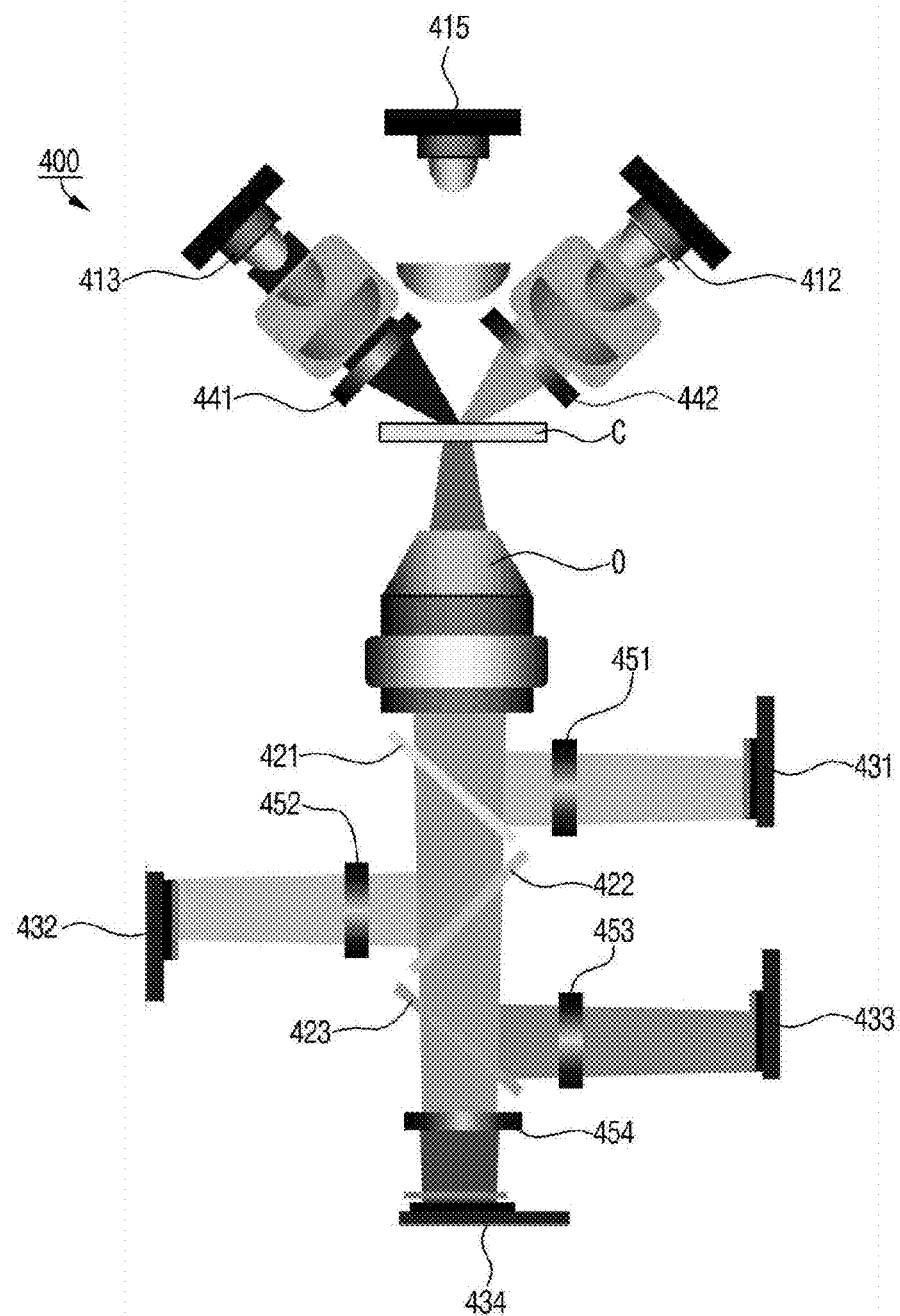
FIG. 14 is a schematic diagram illustrating a fluorescent microscope according to the fourth embodiment of the present invention.
Figure 15:
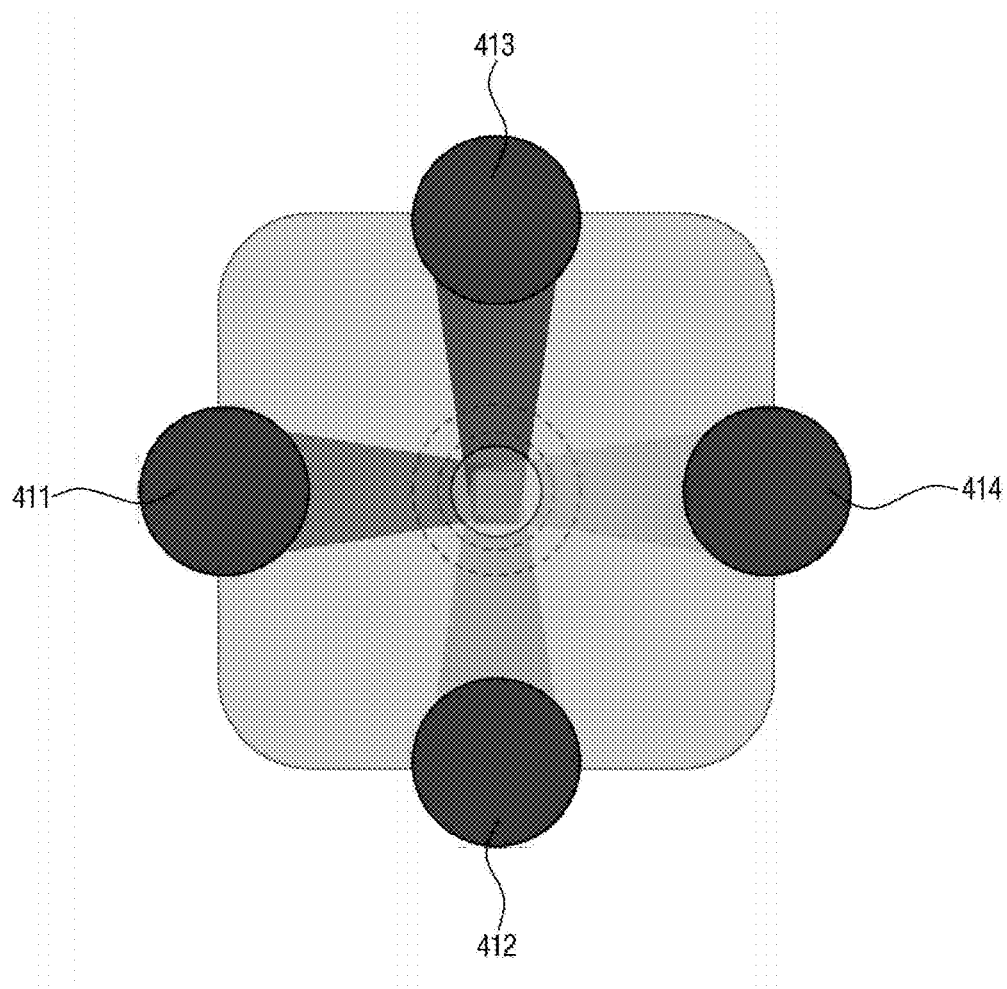
FIG. 15 is a schematic diagram of a light source of the fluorescent microscope of FIG. 14 when viewed from the top.

FIG. 14 is a schematic diagram illustrating a fluorescent microscope according to the fourth embodiment of the present invention. FIG. 15 is a schematic diagram of a light source of the fluorescent microscope of FIG. 14 when viewed from the top.

Referring to the drawings, the fluorescent microscope 400 according to the fourth embodiment of the present invention includes a plurality of light sources 411, 412, 413, and 414 provided to irradiate excitation light having different wavelengths to a survey object C, respectively, a bright field light source 415 provided to obtain a bright field image of the survey object C, a plurality of dichroic filters 421, 422, and 423 provided to reflect only light having short wavelengths of the light provided from the light sources 411, 412, 413, and 414, a plurality of image acquisition units 431, 432, 433, and 434 provided to obtain a fluorescent image of the survey object C by using the light reflected from the dichroic filters 421, 422, and 423, a plurality of excitation filters 441 and 442 provided between the light sources 411, 412, 413, and 414 and the survey object C, a plurality of radiation filters 451, 452, 453, and 454 provided between the dichroic filters 421, 422, and 423 and the image acquisition units 431, 432, 433, and 434 to remove optical noise, and an image processing unit (not illustrated) for adjusting images acquired by the image acquisition units 431, 432, 433, and 444 to reproduce the images into mutually comparable images.

The light sources 411, 412, 413, and 414 are provided above the survey object C such that excitation light having different wavelengths is irradiated to the survey object C. As illustrated in FIG. 14, the light sources 411, 412, 413, and 414 of the present embodiment are realized by LEDs spaced apart from each other by a predetermined interval to inclinedly irradiate excitation light of R (red), G (green), B (blue), and Y (yellow) colors. Further, the bright field light source 415 is realized by white LEDs provided at central portions of the light sources 411, 412, 413, and 414 to obtain a bright field image of the survey object C in the same way as those of the above-described first to third embodiments.

When the surveyor desires to obtain a fluorescent image such as a GFP or an RFP of the survey object C, he or she selectively turns on the corresponding light sources 411, 412, 413, and 414, whereas when the surveyor desires to obtain a bright field image of the survey object C, he or she selectively turns off the light sources 411, 412, 413, and 414 and turns on the bright field light source 415.

Meanwhile, the dichroic filters 421, 422, and 423 are configured to reflect the radiation light radiated from the survey object C through the light supplied from the light sources 411, 412, 413, and 414 to the image acquisition units 431, 432, 433, and 434, respectively. In the present embodiment, the dichroic filter corresponding to the light source 414 provided in the red LED is omitted in the drawings. Further, the dichroic filters 421, 422, and 423 of the present embodiment are provided to adjust optical paths of light sources like in all the other embodiments.

The dichroic filters 421, 422, and 423 are disposed to be spaced apart from each other by a predetermined interval such that a dichroic filter reflecting radiation light having a short wavelength is closer to the survey object C than a dichroic filter reflecting radiation light having a relatively long wavelength. That is, the survey object C radiates green radiation light due to the light source 413 supplying blue light, and the dichroic filter 421 reflecting the green radiation light is located to be closest to the survey object C.

A plurality of image acquisition units 431, 432, 433, and 434 are disposed to be spaced apart from each other such that a fluorescent image of the survey object C can be obtained through the radiation light reflected from the dichroic filters 421, 422, and 423, respectively. The image acquisition units 431, 432, 433, and 434 of the present embodiment are substantially the same as the first image acquisition unit 116 or the second image acquisition unit 124 of the above-described first embodiment, and a repeated description thereof will be omitted.

The excitation filters 441 and 442 are provided between the light sources 411, 412, 413, and 414 and the survey object C, respectively to selectively transmit the excitation light supplied from the light sources 411, 412, 413, and 414, and the radiation filters 451, 452, 453, and 454 are provided between the 421, 422, and 423 and the image acquisition units 431, 432, 433, and 434 to remove optical noise of the radiation light radiated from the survey object C. The items regarding the excitation filters 441 and 442 and the radiation filters 451, 452, 453, and 454 can be seen with reference to the above-described first to third embodiments, a detailed description thereof will be described in detail.

Meanwhile, the image processing unit (not illustrated) has a kind of software configuration for adjusting the images acquired through the image acquisition units 431, 432, 433, and 434. The items regarding the image processing performed by the image processing unit (not illustrated) can be seen with reference to a method of surveying a fluorescent image according to another embodiment of the present invention which will be described below, a detailed description thereof will be omitted.

A process of acquiring a fluorescent image of the survey object C by using the fluorescent microscope 400 of the present invention is as follows.

First, a surveyor turns on the light source 413, that is, a blue LED to irradiate blue light from the light source 413. The first excitation light L1 supplied from the light source 413 is irradiated to the survey object C after passing through the excitation filter 443, and green radiation light is radiated from the survey object C to which the first excitation light L1 is irradiated and passes through the objective lens O.

After green radiation light is reflected by the dichroic filter 421 provided closest to the survey object C, optical noise is removed while the green radiation light passes through the radiation filter 451, and the image acquisition unit 431 can obtain a fluorescent image GFP of the survey object C by using the radiation light.

The principles of obtaining fluorescent images (RFP and the like) with the other light sources 412, 413, and 414 are the same, and a detailed description thereof will be omitted.

The fluorescent microscope 400 of the present embodiment includes the image acquisition units 431, 432, 433, and 434 corresponding to the plurality of light sources 411, 412, 413, and 414, so a plurality of fluorescent images can be simply and promptly surveyed without a mechanical movement.

Figure 16:
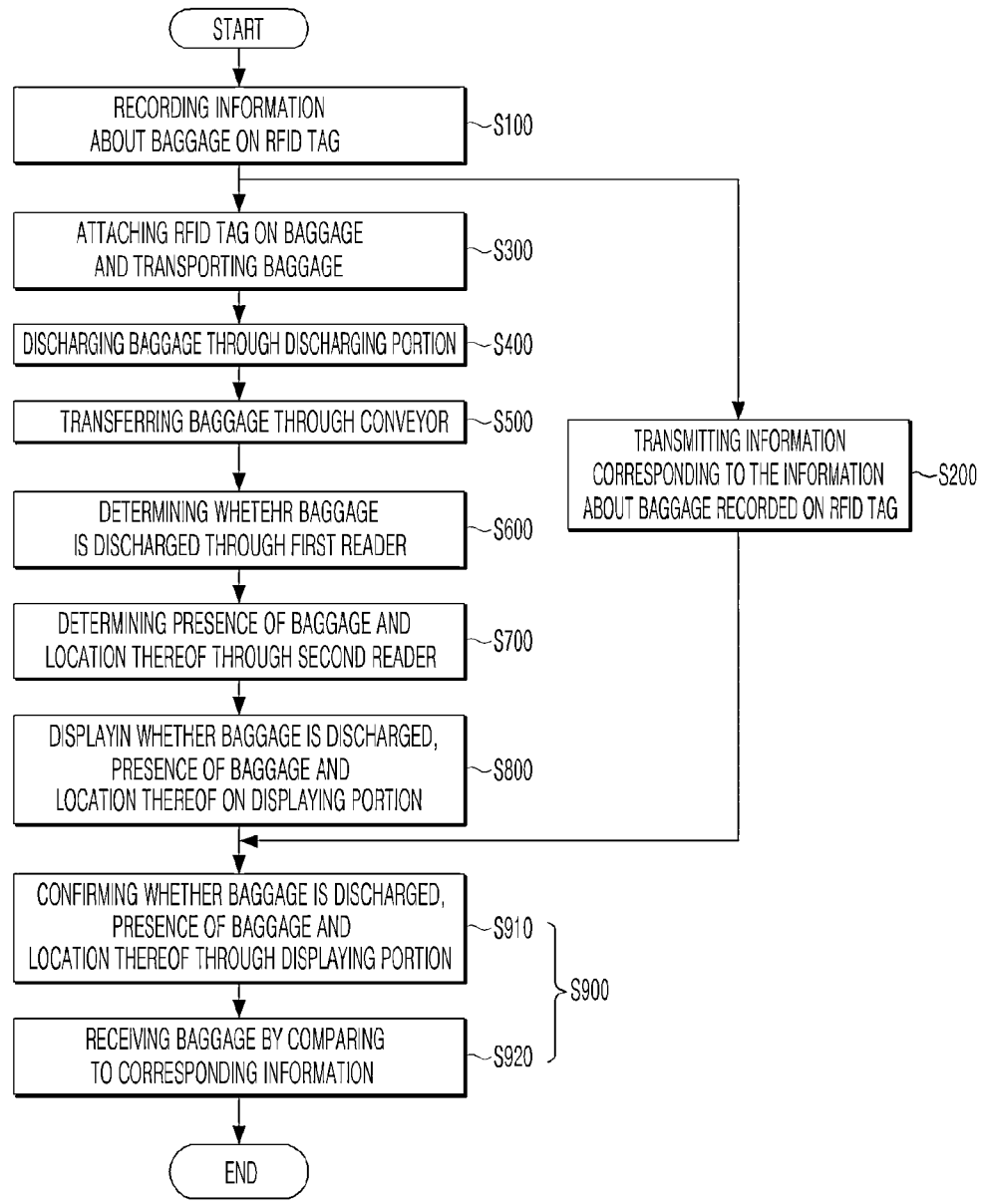
FIG. 16 is a flowchart of a fluorescent image surveying method according to an embodiment of the present invention.

FIG. 16 is a flowchart of a fluorescent image surveying method according to an embodiment of the present invention. FIGS. 17 to 21 are schematic diagrams illustrating a principle of the fluorescent image surveying method of FIG. 16.

The method of surveying a fluorescent image of the present embodiment may be applied to all the fluorescent microscopes of the above-described first to fourth embodiments, and the method of surveying a fluorescent image will be described below based on two images (a GFP and a bright field image) for clarity of description.

As illustrated in FIG. 16, the method of surveying a fluorescent image according to the embodiment of the present invention includes a step S11 of acquiring images of a survey object, respectively, a step S12 of extracting a first center area image forming a central portion of a first image, a step S13 of extracting a second center area image forming a central portion of a second image, a step S14 of comparing the first center area image and the second center area image to extract X and Y displacement values of the second center area image with respect to the first center area image, a step S15 of displacing the second image by using the X and Y displacement values to correct the second image, a step S16 of comparing an outskirt area of the first image and an outskirt area of the second image to extract a direction of a vector, and a step S17 of correcting the second image with reference to the first image, considering the direction of the vector.

The step S11 of acquiring images of a survey object, respectively, is a step of acquiring a GFP image and a bright field image, respectively, by using the fluorescent microscopes 100, 200, 300, and 400 of the above-described first to fourth embodiments.

The step S12 of extracting a first center area image forming a central portion of a first image is a step of extracting a central portion of a bright field image B1 acquired through the fluorescent microscopes 100, 200, 300, and 400, converting the extracted portion to a unicolor image, filter-processing the converted unicolor image, and selecting the filter-processed unicolor image as a first center area image C1, and the step S13 of extracting a second center area image forming a central portion of a second image is a step of extracting a central portion of a GFP image G2 acquired through the fluorescent microscopes 100, 200, 300, and 400, converting the extracted portion to a unicolor image, filter-processing the converted unicolor image, and selecting the filter-processed unicolor image as a second center area image C2. Through the steps S12 and S13, the central portions of the bright field image and the GFP image are extracted and selected as mutually comparable unicolor images.

The step S14 of comparing the first center area image and the second center area image to extract X and Y displacement values of the second center area image with respect to the first center area image is a step of comparing the first center area image C1 and the second center area image C2 and catching a coordinate error value of the second center area image C2 with respect to the first center area image C1.

That is, in the present step S14, by catching a coordinate value (X1, Y1) of one pixel C11 of the first center area image C1 and catching a coordinate value (X2, Y2) of one pixel C21 of the second center area image C2 corresponding thereto, a coordinate error value (X1-X2, Y1-Y2) of the pixel C21 of the second center area image C2 with respect to the pixel C11 of the first center area image C1 is extracted. Here, the extracted coordinate error value (X1-X2, Y1-Y2) corresponds to X and Y displacement values which will be described below.

Of course, in the present step S14, through a process of not only comparing only one pixel C11 or C21 but also comparing a plurality of pixels forming the first center area image C1 and the second center area image C2 to find out an average error value, X and Y displacement values securing certainty are caught.

The step S15 of displacing the second image by using the X and Y displacement values to correct the second image is a step of displacing the entire second image by using the X and Y displacement values found out in the former step S14 to match the GFP image with the bright field image. That is, in the present step S15, the pixels forming the GFP image are disposed at locations closest to the pixels forming the bright field image through adjustment of the entire image area of the GFP image.

The step S16 of comparing an outskirt area of the first image and an outskirt area of the second image to extract a direction of a vector is a step of comparing the first image and the second image once again such that the locations of the pixels forming the second image corrected through the former step S15 may be closest to the locations of the pixels forming the first image, and a step S17 of correcting the second image with reference to the first image, considering the direction of the vector is a step of correcting the second image once again, considering the direction of the vector caught through the former step S16.

In the present steps S16 and S17, the direction of the vector of the pixels contained in the outskirt areas is caught first by comparing the pixel values of the outskirt areas of the first image and the second image, and the second image is corrected through the steps S16 and S17.

Figure 17:
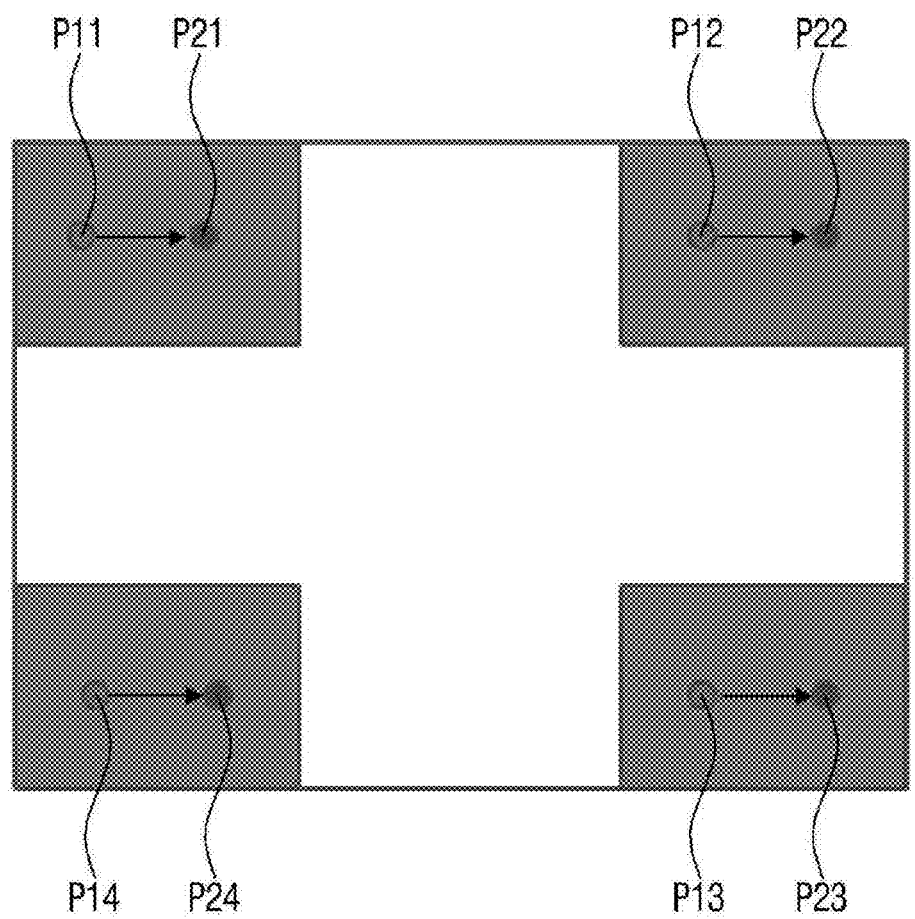
FIGS. 17 to 21 are schematic diagrams illustrating a principle of the fluorescent image surveying method of FIG. 16.

That is, as illustrated in FIG. 17, when the pixels P11, P12, P13, and P14 forming an outskirt area of the first image are compared with the pixels P21, P22, P23, and P24 forming an outskirt area of the second image, if the pixels P21, P22, P23, and P24 of the second image are biased by a predetermined distance to the right side of the pixels P11, P12, P13, and P14 of the first image, the vector direction of the second image with respect to the first image will be the right direction, and thus a correction of the second image is completed by displacing the second image to the left (by adjusting an area of the second image).

Figure 18:
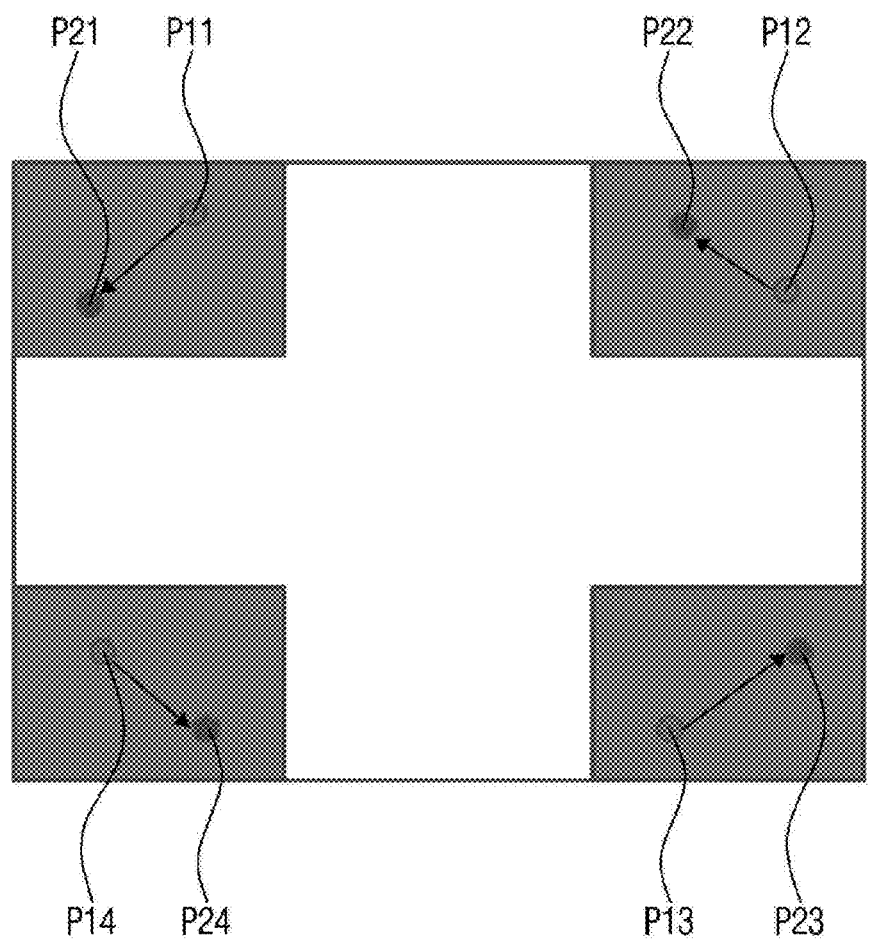

Likewise, as illustrated in FIG. 18, when the pixels P11, P12, P13, and P14 forming an outskirt area of the first image are compared with the pixels P21, P22, P23, and P24 forming an outskirt area of the second image, if the pixels P21, P22, P23, and P24 of the second image are rotated counterclockwise with respect to the pixels P11, P12, P13, and P14 of the first image, the vector direction of the second image with respect to the first image will be a counterclockwise direction, and thus a correction of the second image is completed by displacing the second image clockwise (by adjusting an area of the second image).

Figure 19:
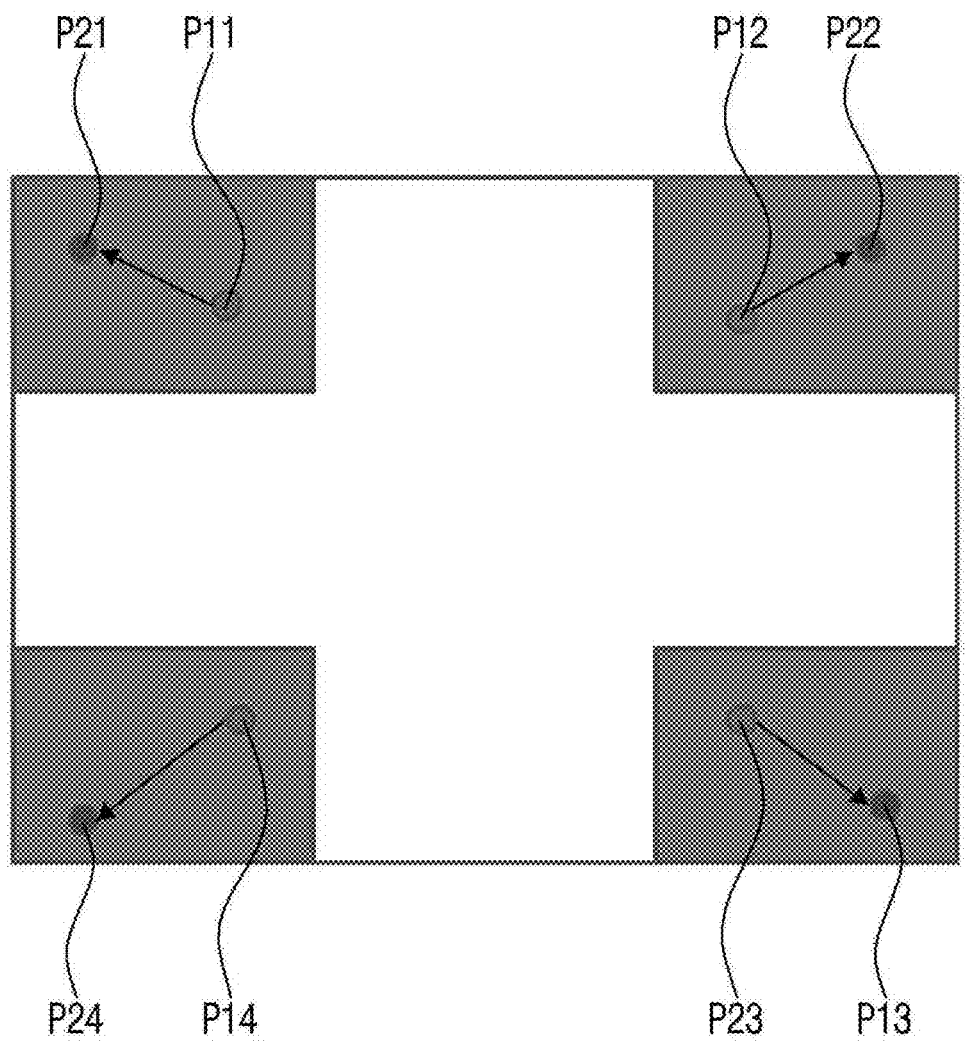
Figure 20:
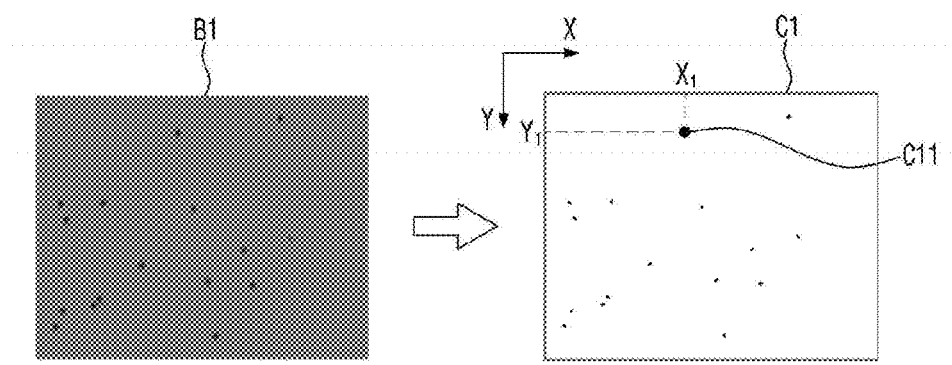
Figure 21:
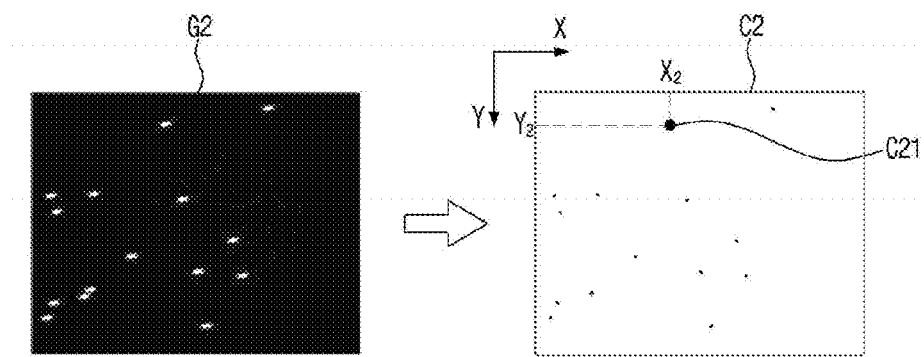

Further, as illustrated in FIG. 19, when the pixels P11, P12, P13, and P14 forming an outskirt area of the first image are compared with the pixels P21, P22, P23, and P24 forming an outskirt area of the second image, if the pixels P21, P22, P23, and P24 of the second image are biased by a predetermined distance toward a corner of the first image, the vector direction of the second image with respect to the first image will be the direction toward the corner, and thus a correction of the second image is completed by displacing the second image in a direction opposite to the direction toward the corner (by adjusting an area of the second image).

Of course, the step S12 of extracting a first center area image forming a central portion of a first image, the step S13 of extracting a second center area image forming a central portion of a second image, the step S14 of comparing the first center area image and the second center area image to extract X and Y displacement values of the second center area image with respect to the first center area image, and the step S15 of displacing the second image by using the X and Y displacement values to correct the second image may be omitted if necessary. That is, if necessary, a correction of the second image may be finished by comparing only the outskirt areas of the first image and the second image.

The step S12 of extracting a first center area image forming a central portion of a first image, the step S13 of extracting a second center area image forming a central portion of a second image, the step S14 of comparing the first center area image and the second center area image to extract X and Y displacement values of the second center area image with respect to the first center area image, and the step S15 of displacing the second image by using the X and Y displacement values to correct the second image may be an independent image correcting method by themselves. That is, if necessary, a correction of the second image may be finished by comparing only the center areas of the first image and the second image.

Since each of the above-described fluorescent microscopes 100, 200, 300, and 400 includes a plurality of image acquisition units (a kind of sensors), an alignment thereof cannot be accurately made due to mechanical tolerances and differences in precisions as the number of sensors increases, and accordingly, in order to solve the problem, in the method of surveying a fluorescent image of the present embodiment, a more precise fluorescent image can be obtained by supplementing images (a GFP image, an RFP image, and a bright field image) obtained through the fluorescent microscopes 100, 200, 300, and 400 in a software fashion.

That is, according to the method of surveying a fluorescent image of the present embodiment, a clearer and more accurate fluorescent image can be obtained by compensating an alignment of images (a GFP image, an RFP image, and a bright field image) obtained through the first to fourth embodiments in a software fashion.

Although the specific embodiments of the present invention have been described and illustrated, the present invention is not limited to the embodiments, but it is apparent to those skilled in the art to which the present invention pertains that the present invention may be variously corrected and modified without departing from the sprit and scope of the present invention. Accordingly, the corrections and modifications should not be understood separately from the technical spirit or aspect of the present invention, and the modified embodiments fall within the scope of the present invention defined by the claims.

The invention claimed is:

1. A fluorescent microscope for observing multiple fluorescent images, the fluorescent microscope comprising:
   at least two or more optical modules, the optical modules comprising,
   a first optical module comprising a first light source for supplying first excitation light having a first wavelength, a first excitation filter for selectively transmitting the first excitation light supplied from the first light source, a first dichroic filter for reflecting the first excitation light having passed through the first excitation filter toward the survey object, an objective lens for condensing the first excitation light reflected by the first dichroic filter and transferring the condensed first excitation light to the survey object, a second dichroic filter for reflecting first radiation light radiated from the survey object, a first radiation filter for selectively transmitting the first radiation light reflected by the second dichroic filter, and a first image acquisition unit for acquiring a first fluorescent image by using the first radiation light having passed through the first radiation filter to be supplied;
   a second optical module comprising a second light source for supplying second excitation light having a second wavelength, a second excitation filter for selectively transmitting the second excitation light supplied from the second light source, a second radiation filter passing through the second excitation filter and irradiated to the survey object to be radiated, to selectively transmitting the second radiation light having passed through the objective lens, the first dichroic filter, and the second excitation filter, and a second image acquisition unit for acquiring a second fluorescent image by using the second radiation light having passed through the second radiation filter to be supplied; and
   a third optical module comprising a third light source provided adjacent to the second light source to supply third excitation light having a third wavelength to the survey object such that a bright field image of the survey object is surveyed through the second image acquisition unit, and a third dichroic filter disposed in a direction perpendicular to a disposition direction of the third dichroic filter between the third light source and the third dichroic filter to uniformly adjust a brightness of the bright field image, wherein
   the fluorescent microscope further comprises an image processing unit for setting coordinate values of images acquired through the first image acquisition unit and the second image acquisition unit, comparing the first and second fluorescent images to detect a coordinate of the same survey object, calculating coordinate errors of other images with reference to a reference image to correct the coordinate values for the first and second fluorescent images, setting effective areas of the images by using the corrected coordinate values, and adjusting the first and second fluorescent images to an image on the effective area according to the set effective area to correct the images, respectively, wherein
   the first and second light sources are selectively turned on when to obtain the first and second fluorescent images of the survey object, and
   the first and second light sources are selectively turned off and the third light source is turned on when to obtain the bright field image of the survey object, and wherein
   a plurality of fluorescent images are surveyed without a mechanical replace of a light source and a filter according to a type of light irradiated to the survey object.

2. The fluorescent microscope as claimed in claim 1, wherein the first light source is a blue solid state fluorescence light source, the second light source is any one of a green solid state fluorescence light source and a red solid state fluorescence light source, and the third light source is any one of a white solid state fluorescence light source and a red solid state fluorescence light source.

3. The fluorescent microscope as claimed in claim 1, wherein the first image acquisition unit and the second image acquisition unit correspond to a charge-coupled device (CCD) image sensor or a complementary metal oxide semiconductor (CMOS) image sensor, respectively.

4. The fluorescent microscope as claimed in claim 1, wherein the first image acquisition unit and the second image acquisition unit independently adjust an exposure time and a fluorescence intensity of a fluorescent image in response to the fluorescent image to be surveyed, respectively.

5. The fluorescent microscope as claimed in claim 1, wherein the first image acquisition unit and the second image acquisition unit independently adjust an exposure time and a fluorescence intensity of a fluorescent image in response to the fluorescent image to be surveyed, respectively.

6. The fluorescent microscope as claimed in claim 1, wherein the image processing unit corrects the images through the steps of;
   acquiring images of a survey object, respectively, by using excitation light having different wavelengths irradiated through a plurality of light sources;
   extracting a first center area image forming a central portion of a first image of the acquired images;
   extracting a second center area image forming a central portion of a second image of the acquired images;
   comparing the first center area image and the second center area image to extract X and Y displacement values of the second center area image with respect to the first center area image; and
   displacing the second image by using the X and Y displacement values to correct the second image.

7. The fluorescent microscope as claimed in claim 1, wherein the image processing unit corrects the images through the steps of;

comparing outskirt areas of a first image and a second image of the acquired images, and extracting a direction of a vector; and correcting the second image with reference to the first image, considering the direction of the vector.

* * * * *